(12) United States Patent
Detjen et al.

(10) Patent No.: US 12,145,908 B2
(45) Date of Patent: Nov. 19, 2024

(54) HYDROCARBON EXTRACTION AND/OR SEPARATION PROCESSES UTILIZING A MEMBRANE SEPARATOR

(71) Applicant: ExxonMobil Chemical Patents Inc., Baytown, TX (US)

(72) Inventors: Todd E. Detjen, Bellaire, TX (US); Chong-Jhoo Wang, Singapore (SG); Robert G. Tinger, Friendswood, TX (US)

(73) Assignee: ExxonMobil Engineering & Technology Company, Baytown, TX (US)

(*) Notice: Subject to any disclaimer, the term of this patent is extended or adjusted under 35 U.S.C. 154(b) by 0 days.

(21) Appl. No.: 18/004,200

(22) PCT Filed: Jul. 7, 2021

(86) PCT No.: PCT/US2021/040602
§ 371 (c)(1),
(2) Date: Jan. 4, 2023

(87) PCT Pub. No.: WO2022/026134
PCT Pub. Date: Feb. 3, 2022

(65) Prior Publication Data
US 2023/0295063 A1 Sep. 21, 2023

Related U.S. Application Data

(60) Provisional application No. 63/059,505, filed on Jul. 31, 2020.

(51) Int. Cl.
*C07C 7/144* (2006.01)
*C07C 7/04* (2006.01)

(52) U.S. Cl.
CPC .............. *C07C 7/144* (2013.01); *C07C 7/04* (2013.01)

(58) Field of Classification Search
CPC .......... C07C 7/144; C07C 7/04; C10G 21/28; C10G 31/11
See application file for complete search history.

(56) References Cited

U.S. PATENT DOCUMENTS 3,723,256 A 3/1973 Thompson
4,039,389 A 8/1977 Christman
(Continued)

FOREIGN PATENT DOCUMENTS

CA 2096439 A1 6/1992
EP 0145126 A2 6/1985
(Continued)

OTHER PUBLICATIONS

International Search Report and Written Opinion received for PCT Application No. PCTUS2021040602, mailing date Oct. 20, 2021, 13 Pages.
(Continued)

*Primary Examiner* — Thuan D Dang

(57) ABSTRACT

A membrane separator comprising a membrane is used to separate various streams in processes for separating aromatic hydrocarbons from non-aromatic hydrocarbons. Such streams can be a lean-solvent stream, a rich-solvent stream, or a hydrocarbon stream comprising both aromatic and non-aromatic hydrocarbons. The membrane separator is advantageously used in combination with an extraction sub-system including a liquid-liquid distillation column and/or an extraction distillation column.

19 Claims, 3 Drawing Sheets

(56) References Cited

U.S. PATENT DOCUMENTS

| | | | |
|---|---|---|---|
| 4,207,174 | A | 6/1980 | Christman |
| 4,234,544 | A | 11/1980 | Christman |
| 4,532,029 | A | 7/1985 | Black et al. |
| 4,571,444 | A | 2/1986 | Black et al. |
| 5,310,480 | A | 5/1994 | Vidueira |
| 5,435,918 | A | 7/1995 | Welmers et al. |
| 6,180,008 | B1 | 1/2001 | White |
| 6,187,987 | B1 | 2/2001 | Chin et al. |
| 6,486,373 | B1 | 11/2002 | Abichandani et al. |
| 6,569,390 | B1 | 5/2003 | Sullivan |
| 7,326,818 | B2 | 2/2008 | Beeckman et al. |
| 7,642,393 | B2 | 1/2010 | Wang et al. |
| 7,663,010 | B2 | 2/2010 | Levin |
| 8,183,424 | B2 | 5/2012 | Levin et al. |
| 10,661,258 | B2 | 5/2020 | Detjen et al. |
| 2010/0270213 | A1 | 10/2010 | Noe |
| 2011/0319688 | A1 | 12/2011 | Ou |
| 2012/0108867 | A1 | 5/2012 | Pilliod et al. |
| 2012/0108868 | A1 | 5/2012 | Pilllod et al. |
| 2013/0274532 | A1 | 10/2013 | Porter |
| 2014/0023563 | A1 | 1/2014 | Ou |
| 2015/0051430 | A1 | 2/2015 | Ou et al. |
| 2017/0081259 | A1 | 3/2017 | Molinier et al. |

FOREIGN PATENT DOCUMENTS

| | | |
|---|---|---|
| WO | 2012/135111 A2 | 10/2012 |
| WO | 2022/026134 A1 | 2/2022 |

OTHER PUBLICATIONS

International Preliminary Report on Patentability received for PCT Application No. PCTUS2021040602, mailing date Feb. 9, 2023, 10 Pages.

Zhang, F., (2015) "Selective Separation of Toluene/n-Heptane by Supported Ionic Liquid Membranes with [Bmim] [BF4]", Chemical Engineering & Technology, vol. 38, No. 2, pp. 355-361.

HYDROCARBON EXTRACTION AND/OR SEPARATION PROCESSES UTILIZING A MEMBRANE SEPARATOR

CROSS-REFERENCE TO RELATED APPLICATIONS

This application is a U.S. national phase application of PCT Application Serial No. PCT/US2021/040602 having a filing date of Jul. 7, 2021, which claims priority to and the benefit of U.S. Provisional Application No. 63/059,505 having a filing date of Jul. 31, 2020, the disclosures of both of which are incorporated herein by reference in their entireties.

FIELD

This disclosure relates to processes, equipment, and systems for separating and/or extracting aromatic hydrocarbons from a mixture feed comprising aromatic and non-aromatic hydrocarbons. In particular, this disclosure relates to processes, equipment and systems for separating/or extracting aromatic hydrocarbons from a mixture feed comprising aromatic and non-aromatic hydrocarbons utilizing a membrane separator. The processes, equipment, and systems of this disclosure are useful, e.g., in producing aromatic hydrocarbon products such as benzene, toluene, xylenes, and non-aromatic hydrocarbon products from a mixture feed comprising aromatic hydrocarbons and non-aromatic hydrocarbons.

BACKGROUND

Aromatic hydrocarbon products, such as benzene, toluene, xylenes, p-xylene, o-xylene, ethylbenzene, and the like, especially those with high purities, are highly valuable industrial commodities useful for the production of other value-added industrial chemicals. In a modern petrochemical plant, aromatic hydrocarbon products are routinely produced by separating a mixture feed comprising one or more such aromatic hydrocarbons and non-aromatic hydrocarbons. One example of such mixture feed is a reformate stream, which can comprise non-aromatic hydrocarbons at a high concentration, e.g., up to 30 wt %, based on the total weight of the reformate stream. Other examples of such mixture feed include primarily aromatic hydrocarbon streams produced from a xylenes isomerization unit, a transalkylation unit, or a toluene disproportionation unit. Many of the non-aromatic hydrocarbons present in the mixture feeds are co-boilers of the target aromatic hydrocarbons. As such, producing aromatic hydrocarbon products such as benzene, toluene, xylenes, p-xylene, o-xylene, and the like, from the mixture feed, especially at a high purity, is difficult and inefficient, if not infeasible, by using conventional distillation processes and equipment.

Solvent-assisted separation processes, such as liquid-liquid extraction processes and extraction distillation processes, have been used in the industry for a long time to separate aromatic hydrocarbons from a mixture feed. In such processes, typically a solvent with high polarity, such as sulfolane, tetraethylene glycol, and the like, is used to contact the mixture feed in an extraction column. Because aromatic hydrocarbon molecules typically exhibit a higher polarity than non-aromatic hydrocarbons under the separation conditions, aromatic hydrocarbons disproportionately distributes into the polar solvent to form an aromatic hydrocarbons-rich-solvent stream, which can be subsequently separated to produce high-purity aromatic hydrocarbons and a hydrocarbon-lean-solvent stream. The hydrocarbon-lean-solvent stream can then be recycled to the extraction column. Thus, during the operation of a continuous aromatic hydrocarbons extraction separation process, a quantity of polar solvent circulates in the system.

Overtime, the hydrocarbon-lean-solvent stream recycled to the extraction column can experience a gradual increase of the concentrations of various contaminants during an operation campaign. Such contaminants can include, among others, saturated and unsaturated heavy hydrocarbons, chlorine-containing compounds, silicon-containing compounds, and the like, produced during the extraction process due to high temperature conditions, and/or introduced through the mixture feed. Such contaminants, especially at a high concentration, can cause corrosion and/or fouling of the vessels, conduits, valves, pumps, and other equipment, necessitating frequent shut-downs and maintenance, and severely curtail the life of the system. Thus, an aromatic hydrocarbons extraction system is frequently equipped with one or more solvent regeneration units and/or stream purification units, such as steam stripping column, sorbent beds, and the like, to reduce contaminants in the hydrocarbon-lean-solvent stream recycled to the extraction column. Alternatively, a portion of the hydrocarbon-lean-solvent stream may be purged from time and time and replaced with fresh solvent feed. All these methods add to significant costs to the capital expenditure of the engineering and construction of a new aromatics plant, and the operation thereof.

Thus, there is a continued need for improvement for reducing contaminants in the hydrocarbon-lean-solvent stream recycled to the extraction column in aromatic hydrocarbon extraction processes, and/or improvement in the overall aromatic hydrocarbon production processes. This disclosure satisfies this and other needs.

SUMMARY

It has been found that in an aromatic hydrocarbon extraction process, a membrane separator can be used to separate a contaminant-containing lean-solvent stream (e.g., a recycle polar solvent stream comprising appreciable quantity of heavy components as a portion of the contaminants) to remove at least a portion of the contaminants in the retentate stream, thereby obtaining a purified lean-solvent stream, which can be preferably recycled to the extraction unit. Additionally, a membrane separator can be used to separate a hydrocarbon stream comprising aromatic hydrocarbons and non-aromatic hydrocarbons to obtain an aromatic hydrocarbon-rich permeate stream and a non-aromatic hydrocarbons-rich retentate stream. Further, a membrane separator can be used to separate a rich-solvent stream to obtain a non-aromatic-hydrocarbons-rich retentate stream and an aromatic-hydrocarbons-rich permeate stream, where the former can be advantageously recycled to the extraction column, and aromatic hydrocarbons can be recovered from the latter. The use of a membrane separator in these processes can be a cost-effective, energy-efficient improvement to existing processes for separating aromatic hydrocarbons.

Thus, a first aspect of this disclosure relates to a process for extracting aromatic hydrocarbons from a mixture feed comprising aromatic hydrocarbons and non-aromatic hydrocarbons. The process can comprise (A-1) feeding the mixture feed into an extraction column. The process can further comprise (A-2) providing a first lean-solvent stream comprising a polar solvent at a concentration of $c(ps)$ wt %, and heavy components at a total concentration of $c(hcom)$ wt %, based on the total weight of the lean-solvent stream, preferably 75≤c(ps)≤99.99. The process can further comprise (A-3) feeding the first lean-solvent stream into a membrane separator, wherein: the membrane separator comprises a vessel having a first volume, a second volume, and a membrane between the first volume and the second volume; the first volume is separated from the second volume by the membrane; the membrane is more permeable to the polar solvent than to the heavy components; and the first lean-solvent stream is fed into the first volume. The process can further comprise (A-4) obtaining a retentate stream exiting the first volume of the membrane separator, wherein the retentate steam is rich in the heavy components relative to the first lean-solvent stream. The process can further comprise (A-5) obtaining a permeate stream exiting the second volume of the membrane separator, wherein the permeate stream is depleted in the heavy components relative to the first lean-solvent stream. The process can further comprise (A-6) feeding at least a portion of the permeate stream into the extraction column.

A second aspect of this disclosure relates to a process for separating a mixture feed comprising aromatic hydrocarbons and non-aromatic hydrocarbons. The process can comprise (B-1) feeding the mixture feed into a membrane separator, wherein: the membrane separator comprises a vessel having a first volume, a second volume, and a membrane between the first volume and the second volume; the first volume is separated from the second volume by the membrane; the membrane is more permeable to the aromatic hydrocarbons than to the non-aromatic hydrocarbons; and the mixture feed is fed into the first volume. The process can further comprise (B-2) obtaining a retentate stream exiting the first volume of the membrane separator, wherein the retentate steam is depleted in the aromatic hydrocarbons and rich in the non-aromatic hydrocarbons relative to the mixture feed. The process can further comprise (B-3) obtaining a permeate stream exiting the second volume of the membrane separator, wherein the permeate stream is rich in the aromatic hydrocarbons and depleted in the non-aromatic hydrocarbons relative to the mixture feed.

A third aspect of this disclosure relates to a process for separating a mixture feed comprising aromatic hydrocarbons and non-aromatic hydrocarbons. The process can comprise (C-1) feeding the mixture feed and a first lean-solvent stream comprising a polar solvent into an extraction column. The process can further comprise (C-2) obtaining an overhead stream and a bottoms stream from the extraction column, wherein the overhead stream is rich in non-aromatic hydrocarbons relative to the mixture feed, the bottoms stream is rich in aromatic hydrocarbons and the polar solvent relative to the mixture feed. The process can further comprise (C-3) feeding at least a portion of the bottoms stream into a membrane separator, wherein: the membrane separator comprises a vessel having a first volume, a second volume, and a membrane between the first volume and the second volume; the first volume is separated from the second volume by the membrane; the membrane is more permeable to the aromatic hydrocarbons than to the non-aromatic hydrocarbons; and the at least a portion of the bottoms stream is fed into the first volume. The process can further comprise (C-4) obtaining a retentate stream exiting the first volume of the membrane separator, wherein the retentate steam is depleted in the aromatic hydrocarbons and rich in the non-aromatic hydrocarbons relative to the bottoms stream. The process can further comprise (C-5) obtaining a permeate stream exiting the second volume of the membrane separator, wherein the permeate stream is rich in the aromatic hydrocarbons and depleted in the non-aromatic hydrocarbons relative to the bottoms stream. The process can further comprise (C-6) feeding at least a portion of the retentate stream to the extraction column.

DETAILED DESCRIPTION

Definitions

Figure 1:
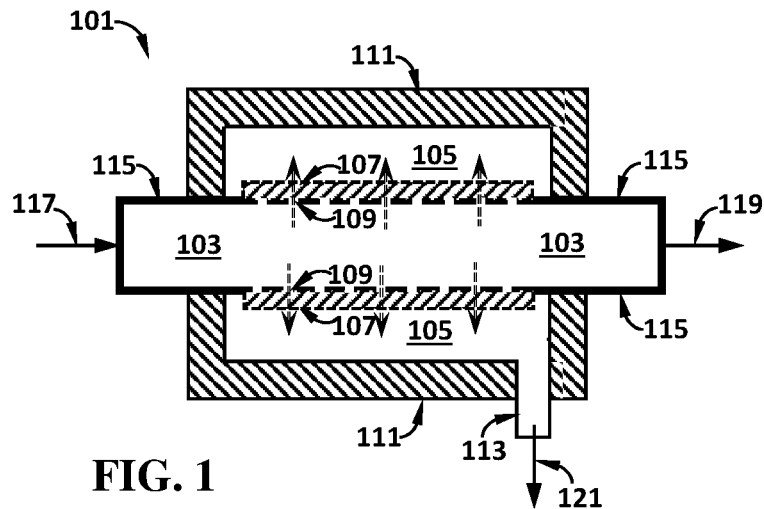
FIG. 1 is a schematic diagram illustrating the structure and operation of a membrane separator useful in embodiments of the processes of this disclosure.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step(s), or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a distillation column" include embodiments where one, two or more distillation columns are used, unless specified to the contrary or the context clearly indicates that only one distillation column is used. Likewise, "a C9+ stream" should be interpreted to include one, two, or more C9+ components, unless specified or indicated by the context to mean only one specific C9+ component.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm", as used herein, are ppm by weight unless specified otherwise. All concentrations herein are expressed on the basis of the total amount of the composition in question. Thus, e.g., the concentrations of the various components of a feed composition are expressed based on the total weight of the feed composition. All ranges expressed herein should include both end points as two specific embodiments unless specified or indicated to the contrary.

"Hydrocarbon" means (i) any compound consisting of hydrogen and carbon atoms or (ii) any mixture of two or more such compounds in (i). The term "Cn hydrocarbon," where n is a positive integer, means (i) any hydrocarbon compound comprising carbon atom(s) in its molecule at the total number of n, or (ii) any mixture of two or more such hydrocarbon compounds in (i). The term "Cn aromatic hydrocarbon," where n is a positive integer, means (i) any aromatic hydrocarbon compound comprising carbon atom(s) in its molecule at the total number of n, or (ii) any mixture of two or more such aromatic hydrocarbon compounds in (i). Thus, a C2 hydrocarbon can be ethane, ethylene, acetylene, or mixtures of at least two of them at any proportion. A "Cm to Cn hydrocarbon" or "Cm-Cn hydrocarbon," where m and n are positive integers and m<n, means any of Cm, Cm+1, Cm+2, Cn−1, Cn hydrocarbons, or any mixtures of two or more thereof. Thus, a "C2 to C3 hydrocarbon" or "C2-C3 hydrocarbon" can be any of ethane, ethylene, acetylene, propane, propene, propyne, propadiene, cyclopropane, and any mixtures of two or more thereof at any proportion between and among the components. A "saturated C2-C3 hydrocarbon" can be ethane, propane, cyclopropane, or any mixture thereof of two or more thereof at any proportion. A "Cm to Cn aromatic hydrocarbon" or "Cm-Cn hydrocarbon," where m and n are positive integers and m<n, means any of Cm, Cm+1, Cm+2, Cn−1, Cn aromatic hydrocarbons, or any mixtures of two or more thereof. A "Cn+hydrocarbon" means (i) any hydrocarbon compound comprising carbon atom(s) in its molecule at the total number of at least n, or (ii) any mixture of two or more such hydrocarbon compounds in (i). A "Cn-hydrocarbon" means (i) any hydrocarbon compound comprising carbon atoms in its molecule at the total number of at most n, or (ii) any mixture of two or more such hydrocarbon compounds in (i). A "Cm hydrocarbon stream" means a hydrocarbon stream consisting essentially of Cm hydrocarbon(s). A "Cm-Cn hydrocarbon stream" means a hydrocarbon stream consisting essentially of Cm-Cn hydrocarbon(s). A "Cn+aromatic hydrocarbon" means (i) any aromatic hydrocarbon compound comprising carbon atom(s) in its molecule at the total number of at least n, or (ii) any mixture of two or more such aromatic hydrocarbon compounds in (i). A "Cn−aromatic hydrocarbon" means (i) any aromatic hydrocarbon compound comprising carbon atoms in its molecule at the total number of at most n, or (ii) any mixture of two or more such aromatic hydrocarbon compounds in (i). A "Cm aromatic hydrocarbon stream" means a hydrocarbon stream consisting essentially of Cm aromatic hydrocarbon(s). A "Cm-Cn aromatic hydrocarbon stream" means a hydrocarbon stream consisting essentially of Cm-Cn aromatic hydrocarbon(s).

An "aromatic hydrocarbon" is a hydrocarbon comprising an aromatic ring in the molecule structure thereof. A "non-aromatic hydrocarbon" means a hydrocarbon other than an aromatic hydrocarbon.

"Co-boiler" means a compound having a normal boiling point in proximity to that of a reference compound or product. For example, where a reference compound or product has a normal boiling point of bp ° C., a co-boiler thereof can have a normal boiling point in the range of bp±30° C., bp±25° C., bp±20° C., bp±15° C., bp±10° C., or bp±5° C. A co-boiler of a reference compound can have a relative volatility in a range from, e.g., 0.5 to 5, or 0.5 to 3, or 0.5 to 2, or 0.5 to 1.5. Typical co-boilers of benzene include, but are not limited to: methylcyclopentane, cyclohexane, 2,3-dimethylpentane, dimethylcyclopentanes, ethylcyclopentane, and 3-methylhexane. Due to close boiling points, conventional distillation typically cannot be economically used to separate co-boilers from a reference compound or product. Major non-aromatic co-boilers of aromatic hydrocarbons present in petrochemical products and petrochemical process streams tend to comprise linear, branched, and/or cyclic alkanes and olefins at total high concentration thereof, e.g., 60 wt %, 70 wt %, 80 wt %, 90 wt %, 95 wt %, or even 98 wt %, based on the total weight of the non-aromatic co-boilers.

"Heavy components" as used herein means components that may be present in a lean-solvent stream differing from the solvent and having a normal boiling point of at least 140° C., e.g., 150° C., 160° C., 180° C., and even 200° C.

"Xylene," either in singular or plural form, shall collectively mean one of or any mixture of two or three of para-xylene, meta-xylene, and ortho-xylene at any proportion thereof.

"Rich" or "enriched" when describing a component in a stream means that the stream comprises the component at a concentration higher than a source material from which the stream is derived. "Depleted" when describing a component in a stream means that the stream comprises the component at a concentration lower than a source material from which the stream is derived. Thus, in embodiments where an admixture stream comprising an aromatic hydrocarbon and a non-aromatic hydrocarbon is separated by a membrane separator comprising a membrane to produce a permeate stream comprising the aromatic hydrocarbon at a higher concentration than the admixture stream and the non-aromatic hydrocarbon at a lower concentration than the admixture stream, the permeate stream is rich or enriched in the aromatic hydrocarbon and depleted in the non-aromatic hydrocarbon relative to the admixture stream.

"Lean" means depleted. A "lean-solvent," or "lean solvent," or "hydrocarbon-lean solvent" in this disclosure interchangeably means a composition or stream depleted in hydrocarbon(s) and consisting essentially of solvent. A "rich-solvent," "rich solvent," or "hydrocarbon-rich solvent" in this disclosure interchangeably means a composition or stream comprising solvent and rich in hydrocarbon(s).

"Consisting essentially of" as used herein means the composition, feed, or effluent comprises a given component at a concentration of at least 60 wt %, preferably at least 70 wt %, more preferably at least 80 wt %, more preferably at least 90 wt %, still more preferably at least 95 wt %, based on the total weight of the composition, feed, or effluent in question.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, 6th Edition, by F. Albert Cotton et al. (John Wiley & Sons, Inc., 1999).

Membrane Separator

A membrane separator useful in the processes according to the various aspects of this disclosure can comprise a vessel having a first volume, a second volume, and a membrane between the first volume and the second volume. The first volume is separate from the second volume by the membrane. An admixture stream comprising a first component and a second component having a lower polarity than the first component is supplied into the first volume. The membrane is selected to have a polarity such that it is more permeable to the first component than to the second component. Thus, on contacting the admixture stream, the membrane preferentially permits the first component to permeate through to enter into the second volume, from which a permeate stream rich in the first component and depleted in the second component relative to the admixture stream exits. A retentate stream exiting the first volume becomes depleted in the first component and rich in the second component relative to the admixture stream. The permeation of component(s) through the membrane is preferentially facilitated by a pressure drop from the first volume to the second volume. Structure and operation of exemplary membrane separator are provided in FIG. 1 and described in greater detail below.

The membrane can be polymer-based. The term polymer includes, but is not limited to, homopolymers, copolymers, terpolymers, polymer blends, and the like. For example, suitable polymers for the membrane include, but are not limited to, polyesters, polyethers, polysulfones, polyimides, polyamides, polymers derived from bisphenol-A dianhydride, polyvinyl alcohols, polyacrylonitriles, polyurethanes, polyureas, polyacrylic acids, polyacrylates, elastomeric polymers such as polybutadiene, polyisoprenes, polyvinylpyridines, halogenated polymers, fluoroelastomers, polyvinyl halides, polysiloxanes, poly dimethyl siloxanes, a copolymer comprising at least one of the foregoing polymers, a blend comprising at least one of the foregoing polymers, an alloy comprising at least one of the foregoing polymers, or a combination comprising at least one of the foregoing polymers, copolymers, blends, or alloys. The polymers could be further physically or chemically ross-linked to increase chemical stability.

In various preferred embodiments, the membrane can be a polyimide-based membrane treated by a lubricating oil. In other embodiments, the membrane can comprise an ionic liquid carried by an organic or inorganic matrix material.

In various preferred embodiments, during operation, the admixture stream supplied into the first volume is in liquid phase. Preferably, during operation, a positive pressure gradient of deltaP kPa exists between the first volume and the second volume, facilitating the permeation of the first component from the first volume into the second volume. Preferably, deltaP can ranges from deltaP1 to deltaP2, where deltaP1 and deltaP2 can be, independently, e.g., 345, 350, 400, 450, 500, 600, 700, 800, 900, 1,000, 1,500, 2,000, 2,500, 3,000, 3,447, 3,500, 4,000, 4,500, 5,000, 5,500, 6,000, 6,500, 7,000, 7,500, 8,000, 8,500, 9,000, 9,500, 10,000, 10,342, as long as deltaP1<deltaP2. Preferably deltaP1=3,447 and deltaP2=8,274.

Description of exemplary membranes, membrane separators, and membrane separation processes useful in the processes of the aspects of this disclosure include, e.g., U.S. Pat. Nos. 4,571,444; 6,187,987; 6,180,008; and 7,642,393; and Zhang, Fan, "Selective Separation of Toluene/n-Heptane by Supported Ionic Liquid Membranes with [Bmim][BF4]," Chem. Eng. Technol. 2015, 38, No. 2, 355-361, the relevant contents in which are incorporated herein by reference.

Liquid-Liquid Extraction Processes for Separating a Mixture Feed Comprising Aromatic Hydrocarbons and Non-Aromatic Hydrocarbons Liquid-liquid extraction ("LLE") processes have been used to separate aromatic hydrocarbons from a mixture comprising aromatic and non-aromatic hydrocarbons. An LLE unit can include a LLE column receiving a feed mixture stream at one location on the column and a polar solvent stream at another location above the feed mixture stream. The solvent stream typically flows downwards to mix with the feed mixture. The polar solvent, e.g., sulfolane, preferentially extracts the aromatic hydrocarbons, due to their higher polarity than the non-aromatic hydrocarbons, to form a rich-solvent stream rich in aromatic hydrocarbons relative to the feed mixture stream exiting the bottom of the column. Non-aromatic hydrocarbons then preferentially flow upwards and exit as an overhead stream. An LLE column is operated at relatively low temperature such that substantially all materials in the column are in liquid phase. An overall LLE unit can also include additional equipment such as one or more stripping column for processing the overhead stream and the rich-solvent stream, and at least one recovery column for recovering high-purity aromatic hydrocarbons from a mixture of the polar solvent and the aromatic hydrocarbons, which also produces a lean-solvent stream. The lean solvent may be partly regenerated and/or cleaned, and then recycled to the LLE column.

Description of exemplary liquid-liquid extraction equipment and process can be found in, e.g., U.S. Pat. Nos. 4,039,389 and 6,569,390, the relevant contents of both of which are incorporated herein by reference.

Extraction Distillation Processes for Separating a Mixture Feed Comprising Aromatic Hydrocarbons and Non-Aromatic Hydrocarbons Extractive distillation ("ED") processes have been used to separate aromatic hydrocarbons from a mixture comprising aromatic and non-aromatic hydrocarbons as well. An ED unit can include an ED column receiving a feed mixture stream at one location on the column and a polar solvent stream at another location above the feed mixture stream. The solvent stream typically flows downwards to mix with the feed mixture. The polar solvent, e.g., sulfolane, preferentially extracts the aromatic hydrocarbons, due to their higher polarity than the non-aromatic hydrocarbons, to form a rich-solvent stream in liquid phase and rich in aromatic hydrocarbons relative to the feed mixture stream exiting the bottom of the column. Non-aromatic hydrocarbons then preferentially flow upwards and exit as an overhead stream in vapor phase. In comparison to an LLE column, an ED column is operated at higher temperature such that the overhead effluent is substantially in vapor phase. An overall ED unit can also include additional equipment such as one or more stripping column for processing the overhead stream and the rich-solvent stream, and at least one recovery column for recovering high-purity aromatic hydrocarbons from a mixture of the polar solvent and the aromatic hydrocarbons, which also produces a lean-solvent stream. The lean solvent may be partly regenerated and/or cleaned, and then recycled to the ED column.

Description of exemplary extraction distillation equipment and process can be found in, e.g., WO2012/135111; U.S. Patent Application Publication No. 20100270213; U.S.

Pat. Nos. 3723256; 4,234,544; 4,207,174; and 5,310,480; the relevant contents of all of which are incorporated herein by reference.

Processes of the First Aspect of this Disclosure

A first aspect of this disclosure relates to process for extracting aromatic hydrocarbons from a mixture feed comprising aromatic hydrocarbons and non-aromatic hydrocarbons, the process comprising:

(A-1) feeding the mixture feed into an extraction column;

(A-2) providing a first lean-solvent stream comprising a polar solvent at a concentration of c(ps) wt %, and heavy components at a total concentration of c(hcom) wt %, based on the total weight of the lean-solvent stream, where 75≤c(ps)≤99.99;

(A-3) feeding the first lean-solvent stream into a membrane separator, wherein: the membrane separator comprises a vessel having a first volume, a second volume, and a membrane between the first volume and the second volume; the first volume is separated from the second volume by the membrane; the membrane is more permeable to the polar solvent than to the heavy components; and the first lean-solvent stream is fed into the first volume;

(A-4) obtaining a retentate stream exiting the first volume of the membrane separator, wherein the retentate steam is rich in the heavy components relative to the first lean-solvent stream;

(A-5) obtaining a permeate stream exiting the second volume of the membrane separator, wherein the permeate stream is depleted in the heavy components relative to the first lean-solvent stream; and (A-6) feeding at least a portion of the permeate stream into the extraction column.

In certain embodiments of the process of the first aspect, the process may further comprise (A-7) phase separating at least a portion of the retentate stream to obtain a heavy components stream and a solvent stream saturated with heavy components; and (A-8) feeding at least a portion of the solvent stream saturated with heavy components to the extraction column. In such embodiments, the solvent stream saturated with heavy components may comprise the heavy components at a total concentration in a range from 3 to 15 wt %, based on the total weight of the solvent stream saturated with the heavy components, e.g., 3 wt %, 4 wt %, 5 wt %, 6 wt %, 7 wt %, 8 wt %, 9 wt %, 10 wt %, 11 wt %, 12 wt %, 13 wt %, 14 wt %, or 15 wt %. The step of phase separating in (A7) can be conveniently carried out in a column receiving the retentate stream at a location between the top and the bottom, and discharging the heavy components stream in the vicinity of the top and the solvent stream saturated with heavy components in the vicinity of the bottom, where the solvent has a higher density than the heavy components. Preferably no additional heat is input into the phase-separating column to effect the phase separation. The heavy components stream can be conducted away as a by-product, or alternatively or additionally separated and processed to produce other products.

The extraction column used in step (A-1) can be a liquid-liquid extraction column or an extraction distillation column described above, or a combination of both. Preferably, the extraction column is an extraction distillation column.

The polar solvent useful in the processes of this disclosure can be any such solvent known in the art. Non-limiting examples of such polar solvent are: tetraethylene glycol, triethylene glycol, diethylene glycol, ethylene glycol, methoxy triglycol ether, diglycolamine, dipropylene glycol, N-formyl morpholine, N-methyl pyrrolidone, 2,3,4,5-tetrahydrothiophene-1, 1-dioxide ("sulfolane"), 3-methylsulfolane and dimethyl sulfoxide, tetramethylenesulfone, mixtures thereof, and/or admixtures with water thereof. A particularly preferred polar solvent is sulfolane.

To facilitate effective and efficient separation in the membrane separator, the first lean-solvent stream can have a temperature T in a range from, e.g., 25 to 80° C. (e.g., 25° C., 26° C., 28° C., 30° C., 35° C., 40° C., 45° C., 50° C., 55° C., 60° C., 70° C., 72° C., 74° C., 75° C., 76° C., 78° C., or 80° C.) when fed into the membrane separator, and a positive pressure gradient of deltaP kPa exists from the first volume to the second volume of the membrane separator, and deltaP can ranges from deltaP1 to deltaP2 kilopascal, where deltaP1 and deltaP2 can be, independently, e.g., 345, 350, 400, 450, 500, 600, 700, 800, 900, 1,000, 1,500, 2,000, 2,500, 3,000, 3,447, 3,500, 4,000, 4,500, 5,000, 5,500, 6,000, 6,500, 7,000, 7,500, 8,000, 8,500, 9,000, 9,500, 10,000, 10,342, as long as deltaP1<deltaP2. Preferably deltaP1=3,447 and deltaP2=8,274.

The first lean-solvent stream can comprise the polar solvent at a concentration of c(ps) wt %, and the heavy components at a total concentration of c(hcom) wt %, based on the total weight of the lean-solvent stream, where c(ps) can range from c(ps)1 to c(ps)2, c(ps)1 and c(ps)2 can be, independently, e.g., 75, 76, 77, 78, 79, 80, 82, 84, 85, 86, 88, 90, 92, 94, 95, 96, 97, 98, 99, 99.9, and 99.99, as long as c(ps)1<c(ps)2; and c(hcom) can range from c(hcom)1 to c(hcom)2, and c(hcom)1 and c(hcom)2 can be, independently, e.g., 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 29, 20, as long as c(hcom)1<c(hcom)2. Preferably c(ps)1≥85 and c(hcom)2≤15. Preferably c(ps)1≥90 and c(hcom)2≤10. Preferably c(ps)1≥92 and c(hcom)2≤8.

In certain embodiments of the process of the first aspect, the process further comprises (A-9) feeding a second lean-solvent stream comprising the polar solvent into the extraction column. In certain specific embodiments, in a given time period, the first lean-solvent stream comprises the polar solvent at a total weight of W1, the second lean-solvent stream comprises the polar solvent at a total weight of W2, and 0.5% W1/(W1+W2)*100% 10%. The value of W1/(W1+W2)*100% may range from v1% to v2%, where v1 and v2 can be, independently, e.g., 0.5, 0.6, 0.7, 0.8, 0.9, 1, 2, 3, 4, 5, 6, 7, 8, 9, 10. Preferably r1=1 and r2=5. Preferably r1=1 and r2=3. In these embodiments, compared to the quantity of the polar solvent supplied directly into the extraction column, W2, the quantity of the polar solvent in the first lean-solvent stream, subjected to membrane separation and purification, W1, is relatively small. In certain specific embodiments, the first lean-solvent stream and the second lean-solvent stream are derived from a common lean-solvent stream, e.g., as two split streams from the common lean-solvent stream. The common lean-solvent stream can be a recycle solvent stream produced from, e.g., a distillation column separating a rich-solvent stream consisting essentially of the polar solvent and aromatic hydrocarbons. Although only a small fraction of the recycle lean-solvent stream is subjected to heavy components abatement using the membrane separator, the cumulative amount of heavy components removed and abated by the membrane separator can be significant over a prolonged operation campaign, capable of significantly increase the service life of the batch of the polar solvent circulating in the extraction system, with or without using additional means to further purify the polar solvent in circulation such as sorbent beds, vacuum regeneration column, and steam stripping solvent regenerator. In certain specific embodiments, where the common lean-solvent stream comprise the heavy components at a total concentration of c(hcom-cs) wt %, based on the total weight of the common lean-solvent stream, and the process further comprises: (A-10) monitoring c(hcom-cs); and (A-11) implementing steps (A-3) to (A-8) only if c(hcom-cs)≥1, e.g., if c(hcom-cs)≥2, if c(hcom-cs)≥3, if c(hcom-cs)≥4, if c(hcom-cs)≥5, if c(hcom-cs)≥6, if c(hcom-cs)≥7, if c(hcom-cs)≥8, if c(hcom-cs)≥9, if c(hcom-cs)≥10, if c(hcom-cs)≥11. In these embodiments, the steps (A-3)-(A-8) are only implemented when the common lean-solvent stream comprises the heavy components at an appreciable concentration, e.g., only after the polar solvent has been circulated in the extraction separation system for a prolonged period of time.

In various embodiments of the process of the first aspect, the process may further comprise: (A-12) obtaining a bottoms stream from the extraction column, wherein the bottoms stream is rich in aromatic hydrocarbons and the polar solvent relative to the mixture feed; (A-13) separating at least a portion of the bottoms stream in a stripping column to obtain an aromatic hydrocarbons-rich stream depleted in the polar solvent relative to the bottoms stream, and a third lean-solvent stream depleted in aromatic hydrocarbons relative to the bottoms stream; and (A-14) deriving at least one of the first lean-solvent stream, the second lean-solvent stream, and the common lean-solvent stream from the third lean-solvent stream. In these embodiments, a circulation loop of the polar solvent exists in the overall process. As discussed above, steps (A3)-(A8), where implemented, function to purity at least a portion of the recycle lean-solvent stream to prolong the service life thereof in the overall process and system. In step (A-13), an optional steam stream may be fed into the stripping column. In step (A-13), a steam-rich overhead stream may be obtained from the stripping column, which can be condensed and separated to obtain a water stream and an oil stream.

In certain specific embodiments comprising steps (A-12) to (A-14), the process may further comprise (A-15) deriving a fourth lean-solvent stream from the third lean-solvent stream; (A-16) regenerating the fourth lean-solvent stream in a steam stripping regeneration column and/or a vacuum regeneration column to obtain a regenerated lean-solvent stream comprising steam and a bottoms heavy stream; and (A-17) feeding the regenerated lean-solvent stream into one or more of: the stripping column, the extraction column, and the membrane separator as at least a portion of the first lean-solvent stream. In these embodiments, a regeneration column is utilized to further purify a lean-solvent stream, further prolonging the service life of the polar solvent in the process. In specific embodiments, the process further comprises (A-18) condensing at least a portion of the aromatic hydrocarbons-rich stream to obtain a mixture comprising an aqueous liquid phase and an oil liquid phase; (A-19) separating the aqueous liquid phase to obtain a water stream; (A-20) heating the water stream to obtain a steam stream; and (A-21) feeding the steam stream to the steam stripping regeneration column. In certain specific embodiments, in step (A-21), the steam stream is at least partly heated by a portion of the third lean-solvent stream.

Compared to using only sorbent beds to purify a polar solvent stream as is known in the art, which consumes the sorbent necessitating periodic sorbent bed change-out, the process of this disclosure using a membrane separator has the advantage of producing much less waste and incurring much lower costs. Compared to using only a steam stripping solvent regenerator or a vacuum regenerator to purify a polar solvent stream as is known in the art, the process of this disclosure using a membrane separator has the advantage of much less energy consumption, producing less waste water, improved abatement of the heavy components from the lean-solvent stream(s) because the capability of a steam regeneration column is limited by the temperature of the steam or the temperature of the vacuum column, and lower rate of degradation of the polar solvent because the membrane separator operates at a much lower temperature than a steam regeneration column or a vacuum regenerator. In addition, the process of this disclosure using a membrane separator has the advantage of ability to separate and abate heavy components co-boiling with the polar solvent or heavier than the polar solvent from the polar solvent, which a process using steam stripping regeneration or vacuum regeneration cannot separate or reduce from the polar solvent.

Processes of the Second Aspect of this Disclosure

A second aspect of this disclosure relates to a process for separating a mixture feed comprising aromatic hydrocarbons and non-aromatic hydrocarbons, the process comprising:

(B-1) feeding the mixture feed into a membrane separator, wherein: the membrane separator comprises a vessel having a first volume, a second volume, and a membrane between the first volume and the second volume; the first volume is separated from the second volume by the membrane; the membrane is more permeable to the aromatic hydrocarbons than to the non-aromatic hydrocarbons; and the mixture feed is fed into the first volume;

(B-2) obtaining a retentate stream exiting the first volume of the membrane separator, wherein the retentate steam is depleted in the aromatic hydrocarbons and rich in the non-aromatic hydrocarbons relative to the mixture feed; and (B-3) obtaining a permeate stream exiting the second volume of the membrane separator, wherein the permeate stream is rich in the aromatic hydrocarbons and depleted in the non-aromatic hydrocarbons relative to the mixture feed.

In certain embodiments of the process of the second aspect, the process further comprises (B-4) feeding at least a portion of the retentate stream and an extraction solvent stream into an extraction sub-system; (B-5) obtaining from the extraction sub-system a non-aromatic hydrocarbons stream, an extracted aromatic hydrocarbons stream, and a lean-solvent stream; and (B-6) recycling at least a portion of the lean-solvent stream into the extraction sub-system as at least a portion of the extraction solvent stream.

In certain embodiments of the process of the second aspect, the process further comprises (B-7) feeding at least a portion of the permeate stream and at least a portion of the extracted aromatic hydrocarbon stream into an aromatic hydrocarbons distillation column; and (B-8) obtaining from the aromatic hydrocarbons distillation column two or more aromatic product streams.

In certain embodiments of the process of the second aspect, the process further comprises (B-9) feeding at least a portion of the permeate stream and/or a least a portion of the extracted aromatic hydrocarbon stream into a reactor; and (B-10) producing a converted product mixture from the reactor.

In certain embodiments of the process of the second aspect, the mixture feed comprises benzene, toluene, C8 aromatic hydrocarbons, non-aromatic hydrocarbon co-boilers of benzene, non-aromatic hydrocarbon co-boilers of toluene, and non-aromatic hydrocarbon co-boilers of C8 aromatic hydrocarbons, at a total concentration thereof ≥60 wt % (e.g., ≥65, ≥70, ≥75, ≥80, ≥85, ≥90, ≥95, ≥98, ≥99, wt %), based on the total weight of the mixture feed.

In certain embodiments of the process of the second aspect, the mixture feed comprises benzene, toluene, non-aromatic hydrocarbon co-boilers of benzene, and non-aromatic hydrocarbon co-boilers of toluene, at a total concentration thereof ≥60 wt % (e.g., ≥65, ≥70, ≥75, ≥80, ≥85, ≥90, ≥95, ≥98, ≥99, wt %), based on the total weight of the mixture feed. Such C6-C7 hydrocarbon mixture feed can be advantageously derived from, e.g., distillation of a C6+ hydrocarbon stream derived from a hydrocarbon reformer comprising, in addition to C6-C7 hydrocarbons, C8, C9, and optionally C9+ hydrocarbons.

In certain embodiments of the process of the second aspect, the mixture feed comprises benzene and non-aromatic hydrocarbon co-boilers of benzene at a total concentration thereof ≥60 wt % (e.g., ≥65, ≥70, ≥75, ≥80, ≥85, ≥90, ≥95, ≥98, ≥99, wt %), based on the total weight of the mixture feed.

In certain embodiments of the process of the second aspect, the mixture feed comprises benzene at a concentration thereof ≥60 wt % (e.g., ≥65, ≥70, ≥75, ≥80, ≥85, ≥90, ≥95, ≥98, ≥99, wt %), based on the total weight of the mixture feed.

In certain embodiments of the process of the second aspect, the mixture feed comprises toluene and non-aromatic hydrocarbon co-boilers of toluene at a total concentration thereof ≥60 wt % (e.g., ≥65, ≥70, ≥75, ≥80, ≥85, ≥90, ≥95, ≥98, ≥99, wt %), based on the total weight of the mixture feed.

In certain embodiments of the process of the second aspect, the mixture feed comprises toluene at a concentration thereof ≥60 wt % (e.g., ≥65, ≥70, ≥75, ≥80, ≥85, ≥90, ≥95, ≥98, ≥99, wt %), based on the total weight of the mixture feed.

In certain embodiments of the process of the second aspect, the process further comprises (B-11) providing an isomerization feed stream consisting essentially of C8 aromatic hydrocarbons; (B-12) contacting the isomerization feed stream with an isomerization catalyst in an isomerization zone under isomerization condition to produce an isomerization product mixture; (B-13) separating the isomerization product mixture to obtain a C7–hydrocarbons-rich stream, and a C8+ hydrocarbon-rich stream; and (B-14) providing at least a portion of the C7– hydrocarbons-rich stream as the at least a portion of the mixture feed. B6a. In certain specific embodiments, the C7– hydrocarbons-rich stream is substantially free of C8 hydrocarbons. In other specific embodiments, the C7– hydrocarbon-rich stream comprises C8 hydrocarbons at a concentration from c(C8)1 to c(C8)2 wt %, based on the total weight of the C7– hydrocarbon-rich stream, where c(C8)1 and c(C8)2 can be, independently, e.g., 0.5, 1, 2, 3, 4, 5, 6, 7, 8, 9, 10, 11, 12, 13, 14, 15, 16, 17, 18, 19, 20. Preferably c(C8)2≤10. Preferably c(C8)2≤5.

The isomerization conditions can include a temperature and a pressure such that a majority of the C8 aromatic hydrocarbons in the isomerization zone are in vapor phase ("vapor-phase isomerization" or "VPI"). Alternatively, the isomerization conditions can include a temperature and a pressure such that a majority of the C8 aromatic hydrocarbons in the isomerization zone are in liquid phase ("liquid-phase isomerization" or "LPI"). LPI requires a lower temperature than VPI, and can be carried out without co-feeding a molecular hydrogen stream into the isomerization zone. As such LPI may be preferred in certain embodiments over VPI, especially where the isomerization feed stream comprises ethylbenzene at a low concentration. The VPI may be favored where the isomerization feed comprises ethylbenzene at a high concentration, e.g., ≥10 wt %, based on the total weight of the isomerization feed stream, because VPI can be more effective than LPI in converting ethylbenzene. Description of exemplary VPI processes and catalysts can be found in, e.g., U.S. Patent Application Publication Nos. US20110319688A1; US20120108867A1; US20120108868A1; US20140023563A1; US20150051430A1; and US20170081259A1; the relevant contents of all of which are incorporated herein by reference. Description of exemplary LPI processes and catalysts can be found in, e.g., U.S. Patent Application Publication Nos. US20110319688A1; US20120108867A1; US20130274532A1; US20140023563A1; and US20150051430A1; the relevant contents of all of which are incorporated herein by reference.

In certain embodiments of the process of the second aspect, the process further comprises (B-15) providing a transalkylation feed mixture comprising C7–aromatic hydrocarbons and C9+ aromatic hydrocarbons; (B-16) contacting the transalkylation feed mixture with a transalkylation catalyst in a transalkylation zone under transalkylation conditions to produce a transalkylation effluent; (B-17) separating the transalkylation effluent to obtain a benzene-rich stream, and a C8 hydrocarbons-rich stream; and (B-18) providing at least a portion of the benzene-rich stream as the at least a portion of the mixture feed. Description of exemplary transalkylation zone, transalkylation catalyst, and transalkylation conditions can be found in, e.g., U.S. Pat. Nos. 7,663,010 and 8,183,424, the relevant contents of both of which are incorporated herein by reference.

In certain embodiments of the process of the second aspect, the process further comprises (B-19) providing a toluene disproportionation feed consisting essentially of toluene; (B-20) contacting the toluene disproportionation feed with a toluene disproportionation catalyst in a disproportionation zone under disproportionation conditions to produce a disproportionation effluent; (B-21) separating the disproportionation effluent to obtain a benzene-rich stream, and a C8 hydrocarbons-rich stream; and (B-22) providing at least a portion of the benzene-rich stream as the at-least a portion of the mixture feed. Description of exemplary disproportionation zone, disproportionation catalysts, and disproportionation conditions can be found in, e.g., U.S. Pat. Nos. 6,486,373; 7,326,818; and 10,661,258; the relevant contents of all of which are incorporated herein by reference. The disproportionation catalyst can be shape-selective or non-shape-selective. If a shape-selective catalyst is used, the disproportionation effluent may comprise p-xylene at a concentration significantly higher than m-xylene and/or o-xylene, and ethylbenzene at a low concentration, based on the total weight of all C8 aromatic hydrocarbons in the disproportionation effluent, which can be highly advantageous for the purpose of co-production of a p-xylene product from the process of the first aspect of this disclosure.

In certain embodiments of the process of the second aspect, the process further comprises (B-23) providing a C6+ hydrocarbons stream comprising benzene, non-aromatic benzene co-boilers, toluene, non-aromatic toluene co-boilers, C8 aromatic hydrocarbons, non-aromatic co-boilers of C8 aromatic hydrocarbons, and C9+ hydrocarbons; (B-24) separating the C6+ hydrocarbons stream to obtain a C7– hydrocarbons stream rich in benzene and toluene, a C7-C8 hydrocarbons stream rich in C8 hydrocarbons, and a C9+ hydrocarbons stream rich in C9+ hydrocarbons; and (B-25) feeding at least a portion of the C7– hydrocarbon stream into the membrane separator as at least a portion of the mixture feed. Such C6+ hydrocarbons stream can be derived from, e.g., an effluent from a hydrocarbons reformer in a petrochemical plant. In specific embodiments, the process may further comprise (B-26) feeding at least a portion of the C7– hydrocarbon stream into the extraction sub-system column.

In certain embodiments of the process of the second aspect, the process further comprises (B-23) conducting away at least a portion of the retentate stream and/or at least a portion of the non-aromatic hydrocarbon stream. In certain specific embodiments, in step (B-23), the at least a portion of the retentate stream and/or the at least a portion of the non-aromatic hydrocarbon stream is used as a mogas blending stock.

In certain embodiments of the process of the second aspect, the process further comprises (B-24) feeding at least a portion of the retentate stream into the extraction sub-system.

Processes of the Third Aspect of this Disclosure

A third aspect of this disclosure relates to a process for separating a mixture feed comprising aromatic hydrocarbons and non-aromatic hydrocarbons, the process comprising:

(C-1) feeding the mixture feed and a first lean-solvent stream comprising a polar solvent into an extraction column;

(C-2) obtaining an overhead stream and a bottoms stream from the extraction column, wherein the overhead stream is rich in non-aromatic hydrocarbons relative to the mixture feed, the bottoms stream is rich in aromatic hydrocarbons and the polar solvent relative to the mixture feed;

(C-3) feeding at least a portion of the bottoms stream into a membrane separator, wherein: the membrane separator comprises a vessel having a first volume, a second volume, and a membrane between the first volume and the second volume; the first volume is separated from the second volume by the membrane; the membrane is more permeable to the aromatic hydrocarbons than to the non-aromatic hydrocarbons; and the at least a portion of the bottoms stream is fed into the first volume;

(C-4) obtaining a retentate stream exiting the first volume of the membrane separator, wherein the retentate steam is depleted in the aromatic hydrocarbons and rich in the non-aromatic hydrocarbons relative to the bottoms stream;

(C-5) obtaining a permeate stream exiting the second volume of the membrane separator, wherein the permeate stream is rich in the aromatic hydrocarbons and depleted in the non-aromatic hydrocarbons relative to the bottoms stream; and (C-6) feeding at least a portion of the retentate stream to the extraction column.

The extraction column may be a liquid-liquid extraction column, an extraction distillation column, a combination of both types.

In various embodiments of the processes of the third aspect, the process may comprise (C-7) obtaining at least an aromatic hydrocarbons-rich stream and a second lean-solvent stream from the permeate stream, wherein the second lean-solvent stream is rich in the polar solvent relative to the permeate steam; and (C-8) recycling at least a portion of the second lean-solvent stream to the extraction column as at least a portion of the first lean-solvent stream. Step (C-7) can be carried out in a single or multiple columns optionally including a stripping column. Where the extraction column is an extraction distillation column, preferably a single distillation column is used in step (C-7), which may be called a "recovery column." Where the extraction column is a liquid-liquid extraction column, step (C-7) can be carried out first by feeding at least a portion of the permeate stream to a striping column, from which a stream rich in non-aromatic hydrocarbons and a bottoms stream rich in aromatic hydrocarbons and the polar solvent are produced. An optional steam stream may be fed into the stripping column. A steam-rich overhead stream may be obtained from the stripping column, which can be condensed and separated to obtain a water stream and an oil stream. The bottoms stream from the stripping column can be then fed into a recovery column from which the aromatic hydrocarbons-rich stream is obtained from the top and the second lean-solvent stream is obtained from the bottom. Additionally or alternatively, where in the extraction column is a liquid-liquid extraction column, at least a portion of the permeate stream may be directly fed to the recovery column as described above.

In certain embodiments of the process of the third aspect, the mixture feed comprises benzene, toluene, C8 aromatic hydrocarbons, non-aromatic hydrocarbon co-boilers of benzene, non-aromatic hydrocarbon co-boilers of toluene, and non-aromatic hydrocarbon co-boilers of C8 aromatic hydrocarbons, at a total concentration thereof ≥60 wt % (e.g., ≥65, ≥70, ≥75, ≥80, ≥85, ≥90, ≥95, ≥98, ≥99, wt %), based on the total weight of the mixture feed.

In certain embodiments of the process of the third aspect, the mixture feed comprises benzene, toluene, non-aromatic hydrocarbon co-boilers of benzene, and non-aromatic hydrocarbon co-boilers of toluene, at a total concentration thereof ≥60 wt % (e.g., ≥65, ≥70, ≥75, ≥80, ≥85, ≥90, ≥95, ≥98, ≥99, wt %), based on the total weight of the mixture feed. Such C6-C7 hydrocarbon mixture feed can be advantageously derived from, e.g., distillation of a C6+ hydrocarbon stream derived from a hydrocarbon reformer comprising, in addition to C6-C7 hydrocarbons, C8, C9, and optionally C9+ hydrocarbons.

In certain embodiments of the process of the third aspect, the mixture feed comprises benzene and non-aromatic hydrocarbon co-boilers of benzene at a total concentration thereof ≥60 wt % (e.g., ≥65, ≥70, ≥75, ≥80, ≥85, ≥90, ≥95, ≥98, ≥99, wt %), based on the total weight of the mixture feed.

In certain embodiments of the process of the third aspect, the mixture feed comprises benzene at a concentration thereof 25 wt % (e.g., ≥25, ≥30, ≥35, ≥40, ≥45, ≥50, ≥55, ≥65, ≥70, ≥75, ≥80, ≥85, ≥90, ≥95, ≥98, ≥99, wt %), based on the total weight of the mixture feed.

In certain embodiments of the process of the third aspect, the mixture feed comprises toluene and non-aromatic hydrocarbon co-boilers of toluene at a total concentration thereof ≥25 wt % (e.g., ≥25, ≥30, ≥35, ≥40, ≥45, ≥50, ≥55, ≥65, ≥70, ≥75, ≥80, ≥85, ≥90, ≥95, ≥98, ≥99, wt %), based on the total weight of the mixture feed.

In certain embodiments of the process of the third aspect, the mixture feed comprises toluene at a concentration thereof ≥60 wt % (e.g., ≤65, ≥70, ≥75, ≥80, ≥85, ≥90, ≥95, ≥98, ≥99, wt %), based on the total weight of the mixture feed.

In certain embodiments of the process of the second aspect, the process further (C-9) providing an isomerization feed stream consisting essentially of C8 aromatic hydrocarbons; (C-10) contacting the isomerization feed stream with an isomerization catalyst in an isomerization zone under isomerization condition to produce an isomerization product mixture; (C-11) separating the isomerization product mixture to obtain a C7–hydrocarbons-rich stream, and a C8+ hydrocarbon-rich stream; and (C-12) providing at least a portion of the C7– hydrocarbons-rich stream as the at least a portion of the mixture feed. In certain specific embodiments, the C7− hydrocarbons-rich stream is substantially free of C8 hydrocarbons. In certain other specific embodiments, the C7− hydrocarbon-rich stream comprises C8 hydrocarbons at a concentration from c(C8)1 to c(C8)2 wt %, based on the total weight of the C7− hydrocarbon-rich stream, where c(C8)1 and c(C8)2 can be, independently, e.g., 0.5, 1, 2, 3, 4, 5, 6, 7, 8, 9, 10, 11, 12, 13, 14, 15, 16, 17, 18, 19, 20. Preferably c(C8)2≤10. Preferably c(C8)2≤5.

The isomerization conditions can include a temperature and a pressure such that a majority of the C8 aromatic hydrocarbons in the isomerization zone are in vapor phase ("vapor-phase isomerization" or "VPI"). Alternatively, the isomerization conditions can include a temperature and a pressure such that a majority of the C8 aromatic hydrocarbons in the isomerization zone are in liquid phase ("liquid-phase isomerization" or "LPI"). LPI requires a lower temperature than VPI, and can be carried out without co-feeding a molecular hydrogen stream into the isomerization zone. As such LPI may be preferred in certain embodiments over VPI, especially where the isomerization feed stream comprises ethylbenzene at a low concentration. The VPI may be favored where the isomerization feed comprises ethylbenzene at a high concentration, e.g., 10 wt %, based on the total weight of the isomerization feed stream, because VPI can be more effective than LPI in converting ethylbenzene. Description of exemplary VPI processes and catalysts can be found in, e.g., U.S. Patent Application Publication Nos. US20110319688A1; US20120108867A1; US20120108868A1; US20140023563A1; US20150051430A1; and US20170081259A1; the relevant contents of all of which are incorporated herein by reference. Description of exemplary LPI processes and catalysts can be found in, e.g., U.S. Patent Application Publication Nos. US20110319688A1; US20120108867A1; US20130274532A1; US20140023563A1; and US20150051430A1; the relevant contents of all of which are incorporated herein by reference.

In certain embodiments of the process of the second aspect, the process further comprises (C-13) providing a transalkylation feed mixture comprising C7−aromatic hydrocarbons and C9+aromatic hydrocarbons; (C-14) contacting the transalkylation feed mixture with a transalkylation catalyst in a transalkylation zone under transalkylation conditions to produce a transalkylation effluent; (C-15) separating the transalkylation effluent to obtain a benzene-rich stream, and a C8 hydrocarbons-rich stream; and (C-16) providing at least a portion of the benzene-rich stream as the at least a portion of the mixture feed. Description of exemplary transalkylation zone, transalkylation catalyst, and transalkylation conditions can be found in, e.g., U.S. Pat. Nos. 7,663,010 and 8,183,424, the relevant contents of both of which are incorporated herein by reference.

In certain embodiments of the process of the second aspect, the process further comprises (C-17) providing a toluene disproportionation feed consisting essentially of toluene; (C-18) contacting the toluene disproportionation feed with a toluene disproportionation catalyst in a disproportionation zone under disproportionation conditions to produce a disproportionation effluent; (C-19) separating the disproportionation effluent to obtain a benzene-rich stream, and a C8 hydrocarbons-rich stream; and (C-20) providing at least a portion of the benzene-rich stream as the at-least a portion of the mixture feed. Description of exemplary disproportionation zone, disproportionation catalysts, and disproportionation conditions can be found in, e.g., U.S. Pat. Nos. 6,486,373; 7,326,818; and 10,661,258, the relevant contents of all of which are incorporated herein by reference. The disproportionation catalyst can be shape-selective or non-shape-selective. If a shape-selective catalyst is used, the disproportionation effluent may comprise p-xylene at a concentration significantly higher than m-xylene and/or o-xylene, and ethylbenzene at a low concentration, based on the total weight of all C8 aromatic hydrocarbons in the disproportionation effluent, which can be highly advantageous for the purpose of co-production of a p-xylene product from the process of the first aspect of this disclosure.

In certain embodiments of the process of the second aspect, the process further comprises (C-21) providing a C6+ hydrocarbons stream comprising benzene, non-aromatic benzene co-boilers, toluene, non-aromatic toluene co-boilers, C8 aromatic hydrocarbons, non-aromatic co-boilers of C8 aromatic hydrocarbons, and C9+ hydrocarbons; (C-22) separating the C6+ hydrocarbons stream to obtain a C7− hydrocarbons stream rich in benzene and toluene, a C7-C8 hydrocarbons stream rich in C8 hydrocarbons, and a C9+ hydrocarbons stream rich in C9+ hydrocarbons; (C-23) feeding at least a portion of the C7− hydrocarbon stream into the membrane separator as at least a portion of the mixture feed. Such C6+ hydrocarbons stream can be derived from, e.g., an effluent from a hydrocarbons reformer in a petrochemical plant. In specific embodiments, the process may further comprise (C-24) feeding at least a portion of the C7− hydrocarbon stream into the extraction sub-system column.

In certain embodiments of the process of the second aspect, the process further comprises obtaining at least one non-aromatic hydrocarbon product stream from the overheads stream. In certain specific embodiments, in step (C-21), at least a portion of the non-aromatic hydrocarbon product stream is used as a mogas blending stock.

Detailed Description of the Processes/Systems Illustrated in FIGS. 1 to 5

FIG. 1 schematically illustrates the cross-sectional structure and operation of a membrane separator useful in embodiments of the processes of this disclosure comprising a vessel 101. Vessel 101 comprises an inner conduit and an outer jacket affixed to and surrounding the outer surface of the inner conduit. Vessel 101 comprises a first volume 103, a second volume 105, and a membrane 107 between volumes 103 and 105. Volume 103 is defined by the inner surface of a wall 115 of the inner conduit. Wall 115 comprises a perforated segment 109 through which fluid can freely pass. The membrane 107 is shown installed on the outer surface of wall 115 covering the perforated segment 109 in FIG. 1, although alternatively or additionally, it may be installed on the inner surface of wall 115. The second volume 105 is defined by the outer surface of wall 115, the outer surface of membrane 107, and the inner surface of the wall 111 of the outer jacket. During operation of the membrane separator, an admixture stream 117 at a first pressure comprising a first component and a second component having a lower polarity than the first component is supplied into the first volume 103 through the inlet end of the inner conduit. The admixture stream then flows along the inner conduit, partly through the perforated segment 109 and then contacts the membrane 107. Due to a pressure drop from the first volume 103 to the second volume 105, a portion of the first component and optionally a portion of the second component pass through the membrane 107 to enter the second volume 105. Without intending to be bound by a particular theory, it is believed that because the first component has higher polarity than the second component, passage of the first component through the membrane 107 is favored over the second component, resulting in the formation of a fluid in the second volume 105 rich in the first component and depleted in the second component relative to admixture stream 117. A portion of the fluid in the second volume 105 exits an outlet 113 as a permeate stream 121. The retentate stream 119 exiting from the first volume 103, shown in FIG. 1 at the outlet end of the inner conduit, is depleted in the first component and rich in the second component relative to the admixture stream 117.

In processes according to the first aspect of this disclosure, the admixture stream 117 can comprise, e.g., a polar solvent as the first component, and a hydrocarbon having a lower polarity than the polar solvent as the second component. Non-limiting examples of the polar solvent can include, e.g., tetraethylene glycol, triethylene glycol, diethylene glycol, ethylene glycol, methoxy triglycol ether, diglycolamine, dipropylene glycol, N-formyl morpholine, N-methyl pyrrolidone, 2,3,4,5-tetrahydrothiophene-1,1-dioxide ("sulfolane"), 3-methylsulfolane and dimethyl sulfoxide, tetramethylenesulfone, mixtures thereof, and/or in admixtures with water thereof. Non-limiting examples of the hydrocarbon can include, aromatic hydrocarbons with various boiling points, non-aromatic hydrocarbons with various boiling points, and mixtures thereof. In a particularly advantageous embodiment, the hydrocarbon comprises heavy hydrocarbons that may contaminate a recycle lean-solvent stream. In these aspects, the polar solvent preferentially passes through the membrane 107 to become enriched in the second volume and the permeate stream and depleted in the retentate stream, and the hydrocarbon(s) preferentially retains and becomes enriched in the first volume and in the retentate stream, and depleted in the second volume and in the permeate stream, relative to the admixture stream.

In specific embodiments of the first aspect, the admixture stream can comprise the polar solvent at a concentration of $c(ps)$ wt %, based on the total weight of the admixture stream, where $c(ps)$ can be in a range from $c(ps)1$ to $c(ps)2$, and $c(ps)1$ and $c(ps)2$ can be, independently, e.g., 75, 78, 80, 82, 84, 85, 86, 88, 90, 92, 94, 95, 96, 98, 99, 99.9, and even 99.99, as long as $c(ps)1 < c(ps)2$. Preferably $c(ps)1=80$, and $c(ps)2=99$. Preferably $c(ps)1=85$, and $c(ps)2=98$. Preferably $c(ps)1=90$, and $c(ps)2=97$. Additionally, the admixture stream can comprise heavy components at a concentration of $c(hcom)$ wt %, based on the total weight of the admixture stream, where $c(hcom)$ can be in a range from $c(hcom)1$ to $c(hcom)2$, and $c(hcom)1$ and $c(hcom)2$ can be, independently, e.g., 0.01, 0.02, 0.04, 0.05, 0.06, 0.08, 0.1, 0.2, 0.4, 0.5, 0.6, 0.8, 1, 2, 4, 5, 6, 8, 10, 12, 14, 15, 16, 18, 20, as long as $c(hcom)1 < c(hcom)2$. Preferably $c(hcom)=0.1$, and $c(hcom)=18$. Preferably $c(hcom)=0.5$, and $c(hcom)=16$. Preferably $c(hcom)=1$, and $c(hcom)=15$. Preferably $c(hcom)=3$, and $c(hcom)=14$. Preferably $c(hcom)=5$, and $c(hcom)=12$.

In processes according to the second aspect of this disclosure, the admixture stream 117 can comprise an aromatic hydrocarbon as the first component, and a non-aromatic hydrocarbon as the second component. Preferably the admixture stream is essentially free of a polar solvent in the admixture stream in those embodiments. Non-limiting examples of such aromatic hydrocarbon can include, e.g., benzene, toluene, xylenes, ethylbenzene, C9 aromatic hydrocarbons, and mixtures of two or more thereof. Non-limiting examples of such non-aromatic hydrocarbons include non-aromatic co-boilers of the aromatic hydrocarbon. Without intending to be bound by a particular theory, it is believed that because an aromatic hydrocarbon tends to exhibit a higher polarity than a non-aromatic hydrocarbon in general, and a non-aromatic hydrocarbon co-boiler thereof in particular, the aromatic hydrocarbon therefore has a higher affinity than the non-aromatic hydrocarbon in general, and the non-aromatic hydrocarbon co-boiler thereof in particular, to the membrane in the membrane separator, and as a result passes through the membrane at a higher speed than the non-aromatic hydrocarbon in general, and the non-aromatic hydrocarbon co-boiler thereof in particular. As a result, the fluid in the second volume and the permeate stream becomes enriched in aromatic hydrocarbon and depleted in the non-aromatic hydrocarbon, and the fluid in the retentate stream becomes enriched in the non-aromatic hydrocarbon and depleted in the aromatic hydrocarbon.

FIG. 2

Figure 2:
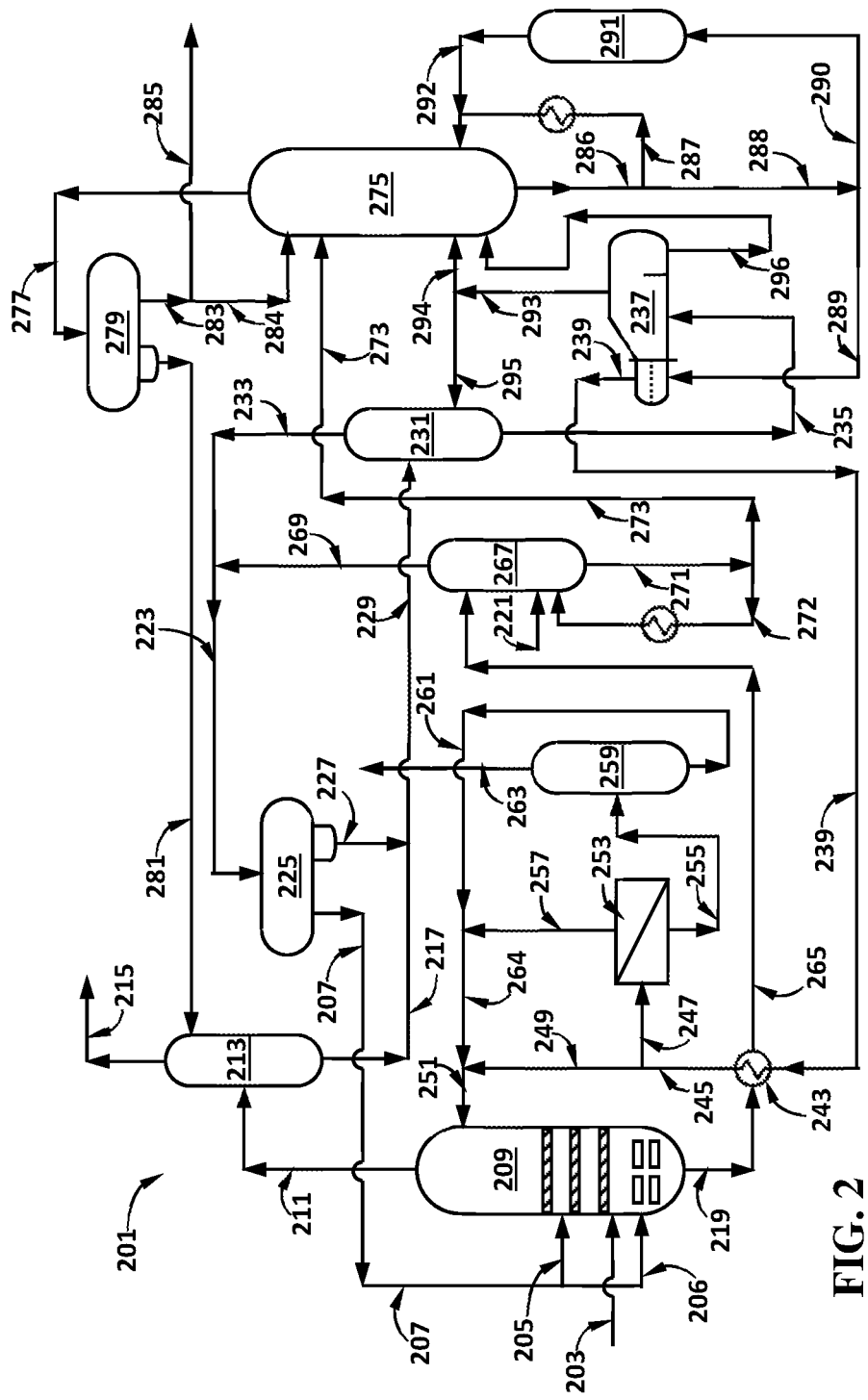
FIG. 2 is a schematic diagram showing an exemplary extraction process/system for separating aromatic hydrocarbons from a mixture feed comprising aromatic hydrocarbons and non-aromatic hydrocarbons including a membrane separator to clean a stream of hydrocarbon-lean solvent, according to an embodiment of the first aspect of this disclosure.

FIG. 2 schematically illustrates an exemplary extraction process/system 201 for separating aromatic hydrocarbons from a mixture feed comprising aromatic hydrocarbons and non-aromatic hydrocarbons using a membrane separator 253 to clean an admixture stream comprising a hydrocarbon-lean solvent, according to an embodiment of the first aspect of this disclosure. As shown in this figure, a first lean polar solvent stream 247 comprising primarily a solvent (e.g., sulfolane) and contaminants (e.g., heavy components) is fed into a membrane separator 253 to produce a permeate stream 253 rich in the solvent and depleted in the contaminants, and a retentate stream 255 rich in the contaminants and depleted in the solvent. The membrane separator 253 may preferably have a structure and be operated in a manner illustrated in FIG. 1 and described in detail above. The permeate stream 257 can then fed into a liquid-liquid extraction column 209 separately (not shown) or optionally after combination with one or more other lean-solvent streams (e.g., streams 249 (a second lean-solvent stream) and 261, as shown) to form a joint stream (stream 251, as shown). The retentate stream 255 can then be fed into a separator 259, from which a stream 263 rich in the contaminants (e.g., heavy components) and depleted in the solvent, and a lean-solvent stream 261 (a third lean-solvent stream) rich in the solvent and depleted in the contaminants are produced. It has been found that, where stream 255 comprises a significant concentration of heavy components achieved by using the membrane separator 253, e.g., a concentration of 5 wt %, based on the total weight of stream 255, phase separation can occur in separator 259 to form a heavy components-rich phase and a solvent-rich phase, conveniently effecting the separation and production of streams 261 and 263 from separator 259. Stream 263 can be conducted away, or optionally after further separation and processing to produce additional products. Stream 261, a thus purified lean-solvent stream, can then be fed into the liquid-liquid extraction column 209, either separately (now shown) or optionally after combination with one or more other lean-solvent streams (e.g., streams 249 and 257, as shown) to form a join stream (stream 251, as shown). Additionally or alternatively, stream 261, or a portion thereof, may be fed into an extraction distillation column (not shown) to facilitate extraction distillation of a mixture feed comprising aromatic hydrocarbons and non-aromatic hydrocarbons. Additionally or alternatively (now shown), stream 261, or a portion thereof, may be fed into a stripping column (e.g., columns 267 and 231, as shown) to facilitate separation. In various embodiments of the processes of the first aspect of this disclosure, by using a membrane separator, a lean-solvent stream containing contaminants (e.g., a recycle lean-solvent stream after a substantial operation period), or a portion thereof, can be conveniently purified under mild conditions with low energy consumption, low maintenance, low capital investment, and low operation costs.

As shown in FIG. 2, the first lean-solvent stream 247 and the second lean-solvent stream 249 can be derived from a common lean-solvent stream 245. Stream 247 can be turned off in certain embodiments, especially where the common stream 245 has a high solvent purity indicated by a relatively low total concentration of the contaminants (e.g., a low total concentration of the heavy components therein, c(hcom-cs) wt %, based on the total weight of stream 245, e.g., where c(hcom-cs)<3, or c(hcom-cs)<1, or c(hcom-cs)<0.5). In those cases purification of a portion of stream 245 by using the membrane separator 253 is not necessary. Thus, in a preferred embodiment, one can monitor the concentration of the contaminants in the common lean-solvent stream 245, e.g., c(hcom-cs), and turn on the first lean-solvent stream 247 only when it reaches a threshold level, e.g., where c(hcom-cs)≥0.5, or c(hcom-cs)≥1, or c(hcom-cs)≥3, or even c(hcom-cs)≥5. Preferably c(hcom-cs)≤20, or c(hcom-cs) ≤18, or c(hcom-cs)≤16, or c(hcom-cs)≤15, or c(hcom-cs) ≤12. As indicated above, at a high concentration of the contaminants in stream 245 and thus stream 247, (e.g., a high c(hcom-cs)), an even higher concentration of the contaminants in retentate stream 255 is achieved, which can conveniently effect a desirable phase separation in separator 259. While it is possible to shut off the second lean-solvent stream 249 completely so that the entirety of stream 245 becomes stream 247 and treated in the membrane separator 253, preferably stream 249 constitutes only a small portion of stream 245. Thus, in preferred embodiments, where in a given time period, the first lean-solvent stream 247 comprises the solvent at a total weight of W1, the second lean-solvent stream 249 comprises the solvent at a total weight of W2, streams 247 and 249 are regulated such that 0.5%≤W1/(W1+W2)*100%≤10%, preferably 0.5%≤W1/(W1+W2)*100%≤8%, preferably 0.5%≤W1/(W1+W2) *100%≤5%, more preferably 1%≤W1/(W1+W2) *100%≤5%, still more preferably 1%≤W1/(W1+W2) *100%≤3%.

The overall process/system of FIG. 2 is now described as follows.

A mixture feed stream 203 comprising aromatic hydrocarbons and non-aromatic hydrocarbons, produced from, e.g., a naphtha reformate stream, a xylenes isomerization effluent stream, a transalkylation effluent stream, a toluene disproportionation effluent stream, or the like, or a mixture thereof, and recycle hydrocarbon streams 205 and 206 derived from a common stream 207, also comprising aromatic hydrocarbons and non-aromatic hydrocarbons, are fed into a liquid-liquid distillation column 209 (alternatively, an extraction distillation column, not shown) at various locations on the column. A recycle lean-solvent stream 251 is fed into column 209 at a location above streams 203, 205, and 206. Inside column 209, the polar solvent admixes with the hydrocarbons and descends to the bottom to produce a rich-solvent stream 219 rich in aromatic hydrocarbons and depleted in non-aromatic hydrocarbons relative to stream 203. From the top, a stream 211 rich in non-aromatic hydrocarbons and depleted in aromatic hydrocarbons relative to stream 203 is produced.

Stream 219, upon being heated at heat exchanger 243 by a recycle lean-solvent stream 239, becomes stream 265 and can be fed into a stripping column 267 optionally along with a steam stream 221 to produce an overhead stream 269 comprising steam and rich in non-aromatic hydrocarbons relative to stream 265 and a bottoms rich-solvent stream 271 rich in aromatic hydrocarbons. Stream 271 can be split into stream 272 for recycling to column 267 and stream 273 for feeding into distillation column 275.

Stream 211 from the top of column 209 can be supplied to a water wash column 213 along with a water-rich stream 281, from which a non-aromatic hydrocarbon stream 215 and an aqueous stream 217 are produced. Stream 215, optionally after additional treatment such as drying and/or separation, can be used or made into various non-aromatic hydrocarbon products, e.g., mogas blending stocks. Stream 217, comprising hydrocarbons and water, can be then fed into a steam stripping column 231, along with a steam stream 295, optionally after combination with other aqueous streams such as stream 227 produced from a phase separator 225 to form a joint stream 229.

From the top of column 231, a hydrocarbon/steam mixture stream 233 and a bottoms stream 235 comprising solvent and water are produced. Stream 233, optionally after combination with stream 269 described above, can be condensed and then phase-separated in phase separator 225 to produce a hydrocarbon stream 207 and an aqueous stream 227. Stream 207 can then be recycled to column 209 as described above. Stream 227 can be combined with stream 217 to form stream 229 as described above. Stream 235 from the bottom of column 231 can then be fed into a steam generator 237, where it is heated by hot lean-solvent stream 289 to produce a steam stream 293 and a solvent-rich stream 296. Steam stream 293 can be split into streams 294 and 295. Stream 295 can be fed into steam stripping column 231 as described above.

Steam stream 294, along with an aromatic hydrocarbons-rich solvent stream 273, solvent-rich stream 296, and an optional lean-solvent stream 292 produced from a solvent regenerator 291, can then be fed into distillation column 275, to produce an aromatic hydrocarbon/steam mixture stream 277 from the top and a hot, lean-solvent stream 286 from the bottom. Stream 277, upon condensing (not shown) is then separated in phase separator 279 to obtain an aqueous stream 281 and an aromatic hydrocarbon stream 283. Stream 281 can be fed to water wash column 213 as described above. Stream 283 can be split into streams 284 recycled to column 275 and stream 285, which, upon optional additional processing such as drying and distillation, can be used as or made into various aromatic hydrocarbon products, e.g., benzene, toluene, benzene/toluene mixture, and the like.

The hot lean-solvent stream 286 exiting the bottom of column 275 can be split into stream 287 for recycling to column 275 upon further heating via a heat exchanger, stream 290 for regeneration in the solvent regenerator 291 to produce a regenerated solvent stream 292, and stream 289 fed into steam generator 237 to heat stream 235 to produce steam stream 293 as described above. The cooled lean-solvent stream 239 exiting steam generator 237 can be further cooled down by the rich-solvent stream 219 produced at the bottom of column 209 at a heat exchanger 243 to form the common lean-solvent stream 245 as described above. Solvent regenerator 291 can be, e.g., a steam stripping column, a vacuum regenerator column, a sorbent bed column containing a bed of a sorbent such as ion exchange resins, inorganic sorbent materials, and combinations thereof. As a result of the use of membrane separator 253 to de-contaminate at least a portion of recycle lean-solvent stream 245 as described above, the solvent regenerator 291, if already existing, can be de-commissioned or operated only intermittently, or not installed or installed with a reduced capacity in a grass-root plant, resulting in savings in equipment investment and/or operation costs.

FIG. 3

Figure 3:
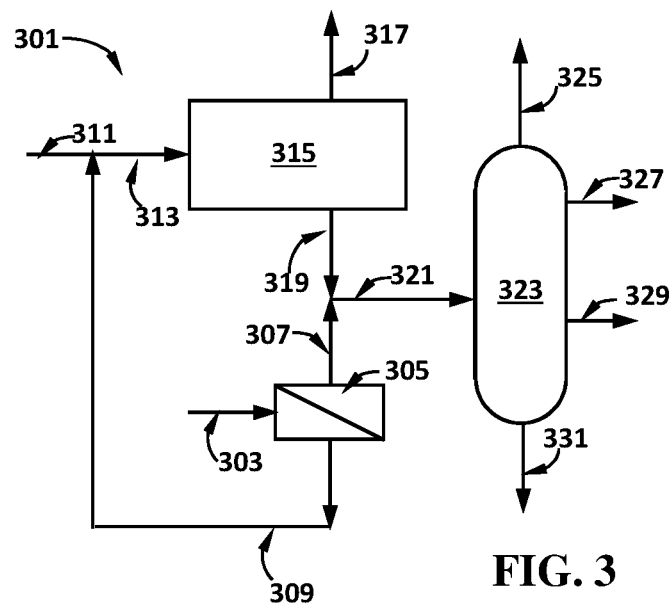
FIGS. 3 and 4 are schematic diagrams showing exemplary extraction processes/systems for separating aromatic hydrocarbons from a mixture feed comprising aromatic hydrocarbons and non-aromatic hydrocarbons using a membrane separator, according to an embodiment of the second aspect of this disclosure.

FIG. 3 schematically illustrates an exemplary extraction process/system 301 for separating aromatic hydrocarbons from a mixture feed comprising aromatic hydrocarbons and non-aromatic hydrocarbons using a membrane separator 305, according to embodiments of the second aspect of this disclosure. As shown in this figure, a mixture feed stream 303 comprising aromatic hydrocarbons and non-aromatic hydrocarbons, e.g., a stream derived from an effluent exiting a C8 aromatic hydrocarbon isomerization unit (not shown), is fed into a membrane separator 305 comprising a membrane between a first and a second volumes, preferably having a structure and operated in a manner illustrated in FIG. 1 as described above, to produce a permeate stream 307 rich in aromatic hydrocarbons and depleted in non-aromatic hydrocarbons relative to stream 303, and a retentate stream 309 rich in non-aromatic hydrocarbons and depleted in aromatic hydrocarbons relative to stream 303. Stream 309 may still comprise aromatic hydrocarbons at various quantity, especially where stream 303 comprises aromatic hydrocarbons at a high concentration, e.g., where stream 303 consists essentially of aromatic hydrocarbons with a total concentration of aromatic hydrocarbons of, e.g., ≥80 wt %, ≥85 wt %, ≥90 wt %, ≥95 wt %, or ≥98 wt %, based on the total weight of stream 303. Stream 309 can then be optionally combined with another mixture feed source stream 311 derived from, e.g., a naphtha reformate stream, to form a joint stream 313, which can then be fed into an extraction separation sub-system 315 to produce a non-aromatic hydrocarbons stream 317 (e.g., a high-purity non-aromatic hydrocarbon stream) and an extracted aromatic hydrocarbons stream 319 (e.g., a high-purity aromatic hydrocarbon stream, preferably a stream essentially free of non-aromatic hydrocarbons). The extraction separation sub-system 315 can comprise, e.g., an extraction column (e.g., an liquid-liquid extraction column, or an extraction distillation column, preferably a liquid-liquid extraction column), one or more stripping columns, an aromatic hydrocarbon-solvent separation distillation column, a lean solvent recycle loop for recycling at least a portion of the lean-solvent stream into the extraction column), and other ancillary equipment, such as those illustrated in FIG. 2 and described above. The two aromatic hydrocarbon streams, the permeate stream 307 from the membrane separator and stream 319 from the extraction separation sub-system 315, can then be combined to form a joint stream 321, which is then fed into an aromatics hydrocarbon separation column 323, from which multiple aromatic product streams such as stream 325 (e.g., a high-purity benzene stream), stream 327 (e.g., a benzene/toluene mixture stream), stream 329 (a high-purity toluene stream), and stream 331 (a C8+ hydrocarbons stream) can be produced. Alternatively or additionally, a portion or the entirety of the retentate stream 309 and/or the non-aromatic hydrocarbons stream 317 can be conducted away and/or made into various products, such as motor gas blending stocks.

A contemplated comparative process/system (not shown) is identical to those of FIG. 3 except that the membrane separator 305 is not installed, and as a result, to remove the non-aromatic hydrocarbons contained in stream 303, the entirety of stream 303 is combined with stream 311 to form stream 313, which is then fed into the extraction sub-system 315. Compared to the comparative process/system, the process/system of FIG. 3 can result in significant savings over time due to much less energy consumption by separating a portion of the aromatic hydrocarbons from stream 303 using the membrane separator and only feeding the non-aromatic hydrocarbons-rich portion 309 thereof into the extraction sub-system 315. The installation of the membrane separator 305 can potentially reduce the capacity required of the extraction sub-system 315 in a grass-root plant resulting in savings in capital expenditure, or enable it to process a larger quantity from stream 311 if the membrane separator 305 is retrofitted into an existing aromatic hydrocarbons production plant resulting in increased productivity. Where stream 303 comprises a high concentration of aromatic hydrocarbons, the process/system of FIG. 3 can be particularly advantageous, because the aromatic hydrocarbons-rich permeate stream 307 can constitute a major portion of stream 303, and only a small portion of stream 303 (i.e., stream 309) is fed into the extraction sub-system 315. In contrast, in the comparative process/system, where stream 303 comprises aromatic hydrocarbons at a high concentration and is nonetheless fed into the extraction sub-system 315 in its entirety, a much larger quantity of aromatic hydrocarbons passes through the extraction sub-system, requiring a higher-capacity extraction sub-system and resulting in significant energy loss.

In a preferred embodiment of the process/system 301, stream 303 can comprise benzene, toluene, non-aromatic hydrocarbon co-boilers of benzene, and non-aromatic hydrocarbon co-boilers of toluene at a total concentration thereof ≥60 wt %, ≥65 wt %, ≥70 wt %, ≥75 wt %, ≥80 wt %, ≥85 wt %, ≥90 wt %, ≥95 wt %, based on the total weight of stream 303. In specific embodiments thereof, stream 303 can comprise benzene and toluene at a total concentration thereof ≥60 wt %, ≥65 wt %, ≥70 wt %, ≥75 wt %, ≥80 wt %, ≥85 wt %, ≥90 wt %, ≥95 wt %, based on the total weight of stream 303. In specific embodiments thereof, stream 303 can comprise benzene at a total concentration thereof ≥60 wt %, ≥65 wt %, ≥70 wt %, ≥75 wt %, ≥80 wt %, ≥85 wt %, ≥90 wt %, ≥95 wt %, based on the total weight of stream 303.

In a preferred embodiment (not shown) of the process/system 301, at least a portion of stream 303 can be produced by: (B-11) providing an isomerization feed stream consisting essentially of C8 aromatic hydrocarbons; (B-12) contacting the isomerization feed stream with an isomerization catalyst in an isomerization zone under isomerization conditions to produce an isomerization product mixture; (B-13) separating the isomerization product mixture to obtain a C7− hydrocarbons-rich stream, and a C8+ hydrocarbon-rich stream; and (B-14) providing at least a portion of the C7− hydrocarbons-rich stream as at least a portion of stream 303. Exemplary C8 aromatic hydrocarbon isomerization processes and systems are described in, e.g., U.S. Patent Application Publication Nos. US20110319688A1; US20120108867A1; US20120108868A1; US20140023563A1; US20150051430A1; and US20170081259A1; the relevant contents of all of which are incorporated herein by reference in their entirety. C8 aromatic hydrocarbon isomerization processes and systems (aka "isomerization units") can be used to convert one or more of ethylbenzene, m-xylene, and o-xylene into more valuable products such as benzene and p-xylene.

In another preferred embodiment (not shown) of the process/system 301, at least a portion of stream 303 can be produced by: (B-15) providing a transalkylation feed mixture comprising C7− aromatic hydrocarbons and C9+ aromatic hydrocarbons; (B-16) contacting the transalkylation feed mixture with a transalkylation catalyst in a transalkylation zone under transalkylation conditions to produce a transalkylation effluent; (B-17) separating the transalkylation effluent to obtain a benzene-rich stream, and a C8 hydrocarbons-rich stream; and (B-18) providing at least a portion of the benzene-rich stream as at least a portion of stream 303. Exemplary transalkylation processes and systems are described in, e.g., U.S. Pat. Nos. 7,663,010 and 8,183,424, the relevant contents of both of which are incorporated herein by reference in their entirety. Transalkylation processes and systems (aka "transalkylation units") can be used to convert C9+ aromatic hydrocarbons and toluene into more valuable products such as benzene and xylenes, particularly p-xylene if combined with an isomerization process/system.

In another preferred embodiment (not shown) of the process/system 301, at least a portion of stream 303 can be produced by: (B-19) providing a toluene disproportionation feed consisting essentially of toluene; (B-20) contacting the toluene disproportionation feed with a toluene disproportionation catalyst in a disproportionation zone under disproportionation conditions to produce a disproportionation effluent; (B-21) separating the disproportionation effluent to obtain a benzene-rich stream, and a C8 hydrocarbons-rich stream; and (B-22) providing at least a portion of the benzene-rich stream as at least a portion of stream 303. Exemplary toluene disproportionation processes and systems are described in, e.g., U.S. Pat. Nos. 7,326,818 and 10,661,258, the relevant contents of both of which are incorporated herein by reference in their entirety. Toluene disproportionation processes and systems (aka "transalkylation units") can be used to convert toluene into more valuable products such as benzene and xylenes, particularly p-xylene.

FIG. 4

Figure 4:
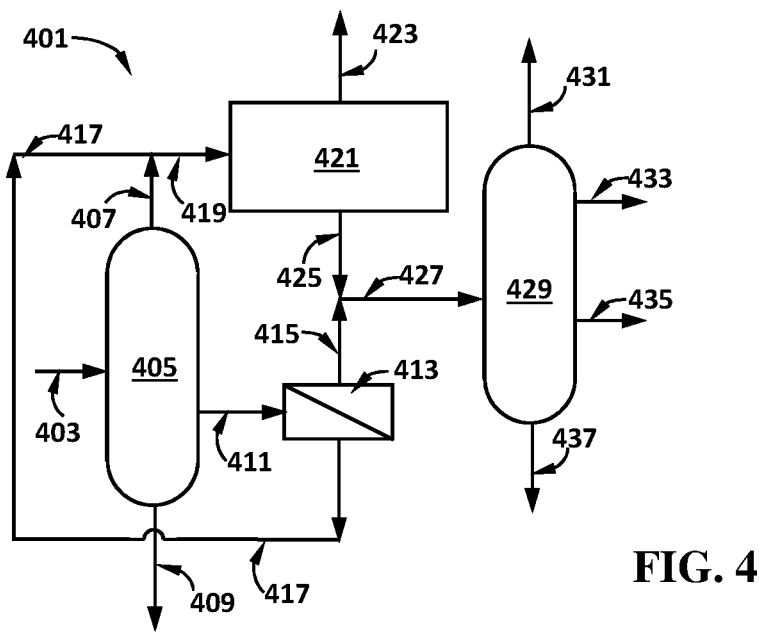

FIG. 4 schematically illustrates an exemplary extraction process/system 401 for separating aromatic hydrocarbons from a mixture feed comprising aromatic hydrocarbons and non-aromatic hydrocarbons using a membrane separator 413, according to embodiments of the second aspect of this disclosure. As shown in this figure, a C6+ hydrocarbons stream 403 comprising benzene, non-aromatic benzene co-boilers, toluene, non-aromatic toluene co-boilers, C8 aromatic hydrocarbons, non-aromatic co-boilers of C8 aromatic hydrocarbons, and C9+ hydrocarbons is fed into a separation column 405 to obtain a C7− hydrocarbons stream 407, a C7−C8 hydrocarbons stream 411, and a C9+ hydrocarbon stream 409. Stream 403 can be derived from a reformate stream produced from a reformer in a petrochemical plant. Stream 407, rich in benzene, benzene co-boilers, toluene, and toluene co-boilers, can be combined with other similar streams, such as stream 417 described below, and then fed into an extraction separation sub-system 421. Stream 409 can be fed into a transalkylation unit (now shown) along with a benzene/toluene stream to produce additional quantity of xylenes. Stream 411, comprising toluene, co-boilers of toluene, C8 aromatic hydrocarbons and co-boilers thereof, can be then fed into a membrane separator 413 comprising a membrane between a first and a second volumes, preferably having a structure and operated in a manner illustrated in FIG. 1 as described above, to produce a permeate stream 415 rich in toluene and C8 aromatic hydrocarbons and depleted in non-aromatic hydrocarbons relative to stream 411, and a retentate stream 417 rich in non-aromatic hydrocarbons and depleted in aromatic hydrocarbons relative to stream 411. Stream 417 may still comprise aromatic hydrocarbons at various quantity, especially where stream 411 comprises aromatic hydrocarbons at a high concentration, e.g., where stream 411 consists essentially of aromatic hydrocarbons with a total concentration of aromatic hydrocarbons of, e.g., $\geq 50$ wt %, $\geq 60$ wt %, $\geq 70$ wt %, $\geq 80$ wt %, $\geq 85$ wt %, $\geq 90$ wt %, $\geq 95$ wt %, or $\geq 98$ wt %, based on the total weight of stream 411. Stream 417 can then be combined with another mixture feed source stream, such as stream 407, to form a joint stream 419, which can then be fed into an extraction separation sub-system 421 to produce a non-aromatic hydrocarbons stream 423 (e.g., a high-purity non-aromatic hydrocarbon stream) and an extracted aromatic hydrocarbons stream 425 (e.g., a high-purity aromatic hydrocarbon stream, preferably a stream essentially free of non-aromatic hydrocarbons). The extraction separation sub-system 421 can comprise, e.g., an extraction column (e.g., an liquid-liquid extraction column, or an extraction distillation column, preferably a liquid-liquid extraction column), one or more stripping columns, an aromatic hydrocarbon-solvent separation distillation column, a lean solvent recycle loop for recycling at least a portion of the lean-solvent stream into the extraction column, and other ancillary equipment, such as those illustrated in FIG. 2 and described above. The two aromatic hydrocarbon streams, the permeate stream 415 from the membrane separator 413 and stream 425 from the extraction separation sub-system 421, can then be combined to form a joint stream 427 and fed into an aromatics hydrocarbon separation column 429, from which multiple aromatic product streams such as stream 431 (e.g., a high-purity benzene stream), stream 433 (e.g., a benzene/toluene mixture stream), stream 435 (a high-purity toluene stream), and stream 437 (a C8 aromatic hydrocarbons stream) can be produced. These various aromatic hydrocarbon streams can be used as high-quality feeds for various downstream processes, e.g., transalkylation, xylene isomerization, toluene disproportionation, benzene/toluene methylation for making xylenes, and the like. Alternatively or additionally, a portion or the entirety of the retentate stream 417 and/or the non-aromatic hydrocarbons stream 423 can be conducted away and/or made into various products, such as motor gas blending stocks.

A contemplated first comparative process/system (not shown) to that of FIG. 4 is identical to that of FIG. 4 except that the membrane separator 413 is not present, and stream 411 is fed into a second extraction separation sub-system (now shown) to produce another aromatic hydrocarbon stream and another non-aromatic hydrocarbon stream. The other aromatic hydrocarbon stream can then be fed into column 429 together with stream 425. Compared to the process/system of FIG. 4, this first comparative process/system requires much more equipment, costs significantly higher, and consumes more energy.

A contemplated second comparative process/system (not shown) to those of FIG. 4 is identical to those of FIG. 4 except that the membrane separator 413 is not present, and stream 411 is fed directly into a downstream process such as isomerization, disproportionation, and the like. Stream 411 contains significant amount of non-aromatics and therefore is inferior to high-quality streams 433, 435, and 437 which contain less or close to no non-aromatic hydrocarbons, for downstream processes. As such, this second comparative process/system can cause undesirable side reactions and produce undesirable by-products and result in less efficiency, lower process stability, shorter process runtime, and the like, to the downstream processes, compared to the process/system of FIG. 4.

FIG. 5

Figure 5:
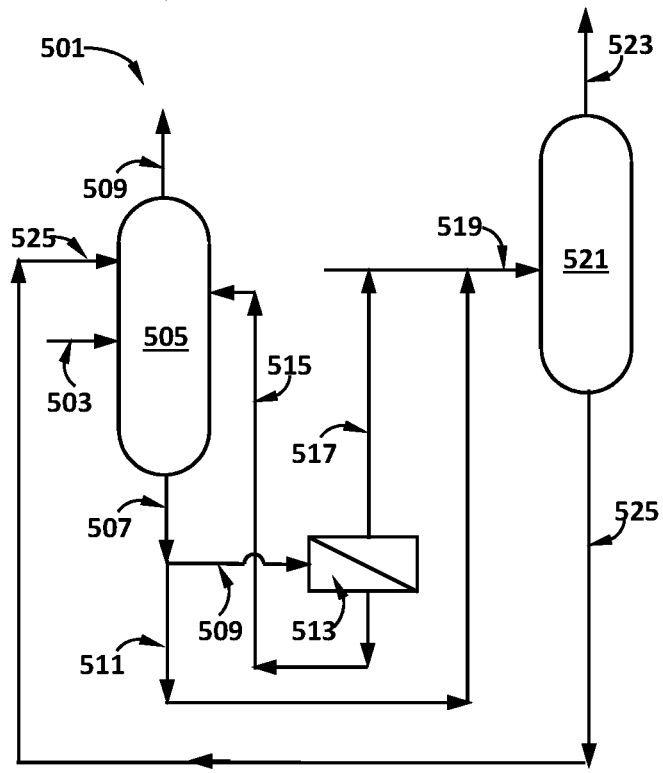
FIG. 5 is a schematic diagram showing an exemplary extraction process/system for separating aromatic hydrocarbons from a mixture feed comprising aromatic hydrocarbons and non-aromatic hydrocarbons using a membrane separator, according to an embodiment of the third aspect of this disclosure.

FIG. 5 schematically illustrates an exemplary extraction process/system 501 for separating aromatic hydrocarbons from a mixture feed comprising aromatic hydrocarbons and non-aromatic hydrocarbons using a membrane separator 511, according to an embodiment of the third aspect of this disclosure. As shown in this figure, a mixture feed stream 503 comprising aromatic hydrocarbons and non-aromatic hydrocarbons, e.g., a stream derived a reformate effluent stream (not shown), is fed into an extraction column 505 (e.g., a liquid-liquid extraction column or an extraction distillation column, preferably a liquid-liquid extraction column), along with a lean-solvent stream 525 and a recycle hydrocarbon-containing stream 515 described below. From column 505, an overhead stream 509 rich in non-aromatic hydrocarbons and depleted in aromatic hydrocarbons relative to stream 503, and a bottoms rich-solvent stream 507 rich in aromatic hydrocarbons and depleted in non-aromatic hydrocarbons are produced. To achieve a high degree of extraction of aromatic hydrocarbons in column 505, the process may be configured such that stream 507 nonetheless comprises substantial quantity of non-aromatic hydrocarbons and stream 509 can be substantially free of aromatic hydrocarbons. A split stream 509 from stream 507 (as shown) or the entirety of stream 507 can be then fed into a membrane separator 513 comprising a membrane between a first and a second volumes, preferably having a structure and operated in a manner in FIG. 1 as described above, to produce a permeate stream 517 rich in aromatic hydrocarbons and depleted in non-aromatic hydrocarbons relative to stream 509, and a retentate stream 515 rich in non-aromatic hydrocarbons and depleted in aromatic hydrocarbons relative to stream 509. Stream 515 may nonetheless comprise aromatic hydrocarbons at a substantial quantity, in addition to the solvent and non-aromatic hydrocarbons. Thus stream 515 is preferably recycled back to column 505, from which aromatic hydrocarbons can be extracted. Stream 517, depleted in non-aromatic hydrocarbons relative to stream 509 and comprising the solvent, can then be fed into an aromatic hydrocarbons/solvent separation sub-system 521, which can comprise, e.g., a distillation column and optional equipment such as a stripping column (not shown). From the separation sub-system 521, a high-purity aromatic hydrocarbons stream 523 and a lean-solvent stream 525 (a second lean-solvent stream) are produced. The second lean-solvent stream 525, or a portion thereof, can then be recycled to the extraction column 505. A portion or the entirety of the non-aromatic hydrocarbons stream 509 can be conducted away and/or made into various products, such as motor gas blending stocks. Stream 523 can be further separated to make one or more aromatic hydrocarbon streams (e.g., a high-purity benzene stream, a toluene-benzene mixture stream, a toluene stream, and the like).

A contemplated comparative process/system (not shown) is identical to those of FIG. 5 except that the membrane separator 513 is not installed and the entirety of stream 507 is fed into aromatic hydrocarbons/solvent separation sub-system 521. Compared to the comparative process/system, the process/system of FIG. 5 can result in significant savings over time due to much less energy consumption by separating a portion of the aromatic hydrocarbons from stream 507 using the membrane separator and only feeding the aromatic hydrocarbons-rich portion 517 thereof into the separation sub-system 521. The installation of the membrane separator 305 can potentially reduce the capacity and number of equipment required of the separation sub-system 521 in a grass-root plant resulting in savings in capital expenditure, or enable it to process a larger quantity from stream 519 if the membrane separator 513 is retrofitted into an existing aromatic hydrocarbons production plant resulting in increased productivity. Where stream 507 comprises a relatively high concentration of non-aromatic hydrocarbons, the process/system of FIG. 5 can be particularly advantageous, because the non-aromatic hydrocarbons-rich retentate stream 515 can constitute a significant portion of stream 507, and only a significantly smaller portion of stream 507 (i.e., stream 517) is fed into the extraction sub-system 521. In contrast, in the comparative process/system, where stream 507 comprises non-aromatic hydrocarbons at a significant concentration and is nonetheless fed into the separation sub-system 521 in its entirety, a much larger quantity of non-aromatic hydrocarbons needs to be separated in the separation sub-system 521, requiring a higher-capacity extraction sub-system 521 with more equipment (e.g., stripping column) and resulting in significant energy loss.

In a preferred embodiment of the process/system 501, stream 503 can comprise benzene, toluene, non-aromatic hydrocarbon co-boilers of benzene, and non-aromatic hydrocarbon co-boilers of toluene at a total concentration thereof $\geq 60$ wt %, $\geq 65$ wt %, $\geq 70$ wt %, $\geq 75$ wt %, $\geq 80$ wt %, $\geq 85$ wt %, $\geq 90$ wt %, $\geq 95$ wt %, based on the total weight of stream 303. In specific embodiments thereof, stream 503 can comprise benzene and toluene at a total concentration thereof $\geq 25$ wt %, $\geq 30$ wt %, $\geq 35$ wt %, $\geq 40$ wt %, $\geq 45$ wt %, $\geq 50$ wt %, $\geq 55$ wt %, $\geq 60$ wt %, $\geq 65$ wt %, $\geq 70$ wt %, $\geq 75$ wt %, $\geq 80$ wt %, $\geq 85$ wt %, $\geq 90$ wt %, $\geq 95$ wt %, based on the total weight of stream 303. In specific embodiments thereof, stream 303 can comprise benzene at a total concentration thereof $\geq 25$ wt %, $\geq 30$ wt %, $\geq 35$ wt %, $\geq 40$ wt %, $\geq 45$ wt %, $\geq 50$ wt %, $\geq 55$ wt %, $\geq 60$ wt %, $\geq 65$ wt %, $\geq 70$ wt %, $\geq 75$ wt %, $\geq 80$ wt %, $\geq 85$ wt %, $\geq 90$ wt %, $\geq 95$ wt %, based on the total weight of stream 303.

In a preferred embodiment (now shown) of the process/system 501, at least a portion of stream 503 can be produced by: (C-9) providing an isomerization feed stream consisting essentially of C8 aromatic hydrocarbons; (C-10) contacting the isomerization feed stream with an isomerization catalyst under isomerization condition to produce an isomerization product mixture; (C-11) separating the isomerization product mixture to obtain a C7− hydrocarbons-rich stream, and a C8+ hydrocarbon-rich stream; and (C-12) providing at least a portion of the C7− hydrocarbons-rich stream as the at least a portion of stream 503.

In another preferred embodiment (not shown) of the process/system 501, at least a portion of stream 503 can be produced by: (C-13) providing a transalkylation feed mixture comprising C7− aromatic hydrocarbons and C9+ aromatic hydrocarbons; (C-14) contacting the transalkylation feed mixture with a transalkylation catalyst under transalkylation conditions to produce a transalkylation effluent; (C-15) separating the transalkylation effluent to obtain a benzene-rich stream, and a C8 hydrocarbons-rich stream; and (C-16) providing at least a portion of the benzene-rich stream as the at least a portion of stream 503.

In another preferred embodiment (not shown) of the process/system 501, at least a portion of stream 503 can be produced by: (C-17) providing a toluene disproportionation feed consisting essentially of toluene; (C-18) contacting the toluene disproportionation feed with a toluene disproportionation catalyst under disproportionation conditions to produce a disproportionation effluent; (C-19) separating the disproportionation effluent to obtain a benzene-rich stream, and a C8 hydrocarbons-rich stream; and (C-20) providing at least a portion of the benzene-rich stream as the at least a portion of stream 503.

In yet another preferred embodiment (not shown) of the process/system 501, at least a portion of stream 503 can be produced by: (C-21) providing a C6+ hydrocarbons stream comprising benzene, non-aromatic benzene co-boilers, toluene, non-aromatic toluene co-boilers, C8 aromatic hydrocarbons, non-aromatic co-boilers of C8 aromatic hydrocarbons, and C9+ hydrocarbons; (C-22) separating the C6+ hydrocarbons stream to obtain a C7− hydrocarbons stream rich in benzene and toluene, a C7− C8 hydrocarbons stream rich in C8 hydrocarbons, and a C9+ hydrocarbons stream rich in C9+ hydrocarbons; and (C-23) feeding at least a portion of the C7− hydrocarbon stream into the membrane separator as the at least a portion of the mixture feed at least a portion of stream 503.

This disclosure can include one or more of the following non-limiting aspects and/or embodiments.

Listing of Embodiments

A1. A process for extracting aromatic hydrocarbons from a mixture feed comprising aromatic hydrocarbons and non-aromatic hydrocarbons, the process comprising:
  (A-1) feeding the mixture feed into an extraction column;
  (A-2) providing a first lean-solvent stream comprising a polar solvent at a concentration of c(ps) wt %, and heavy components at a total concentration of c(hcom) wt %, based on the total weight of the lean-solvent stream, where 75≤c(ps)≤99.99;
  (A-3) feeding the first lean-solvent stream into a membrane separator, wherein: the membrane separator comprises a vessel having a first volume, a second volume, and a membrane between the first volume and the second volume; the first volume is separated from the second volume by the membrane; the membrane is more permeable to the polar solvent than to the heavy components; and the first lean-solvent stream is fed into the first volume;
  (A-4) obtaining a retentate stream exiting the first volume of the membrane separator, wherein the retentate steam is rich in the heavy components relative to the first lean-solvent stream;
  (A-5) obtaining a permeate stream exiting the second volume of the membrane separator, wherein the permeate stream is depleted in the heavy components relative to the first lean-solvent stream; and
  (A-6) feeding at least a portion of the permeate stream into the extraction column.
A2. The process of A1, further comprising:
  (A-7) phase separating at least a portion of the retentate stream to obtain a heavy components stream and a solvent stream saturated with heavy components; and
  (A-8) feeding at least a portion of the solvent stream saturated with heavy components to the extraction column.
A3. The process of A2, wherein the solvent stream saturated with heavy components comprises the heavy components at a total concentration in a range from 3 to 15 wt %, based on the total weight of the solvent stream saturated with the heavy components.
A4. The process of any of A1 to A3, wherein:
  the extraction column is an extraction distillation column.
A5. The process of any of A1 to A4, wherein:
  the extraction column is a liquid-liquid extraction column.
A6. The process of any of A1 to A5, wherein:
  the polar solvent is selected from tetraethylene glycol, triethylene glycol, diethylene glycol, ethylene glycol, methoxy triglycol ether, diglycolamine, dipropylene glycol, N-formyl morpholine, N-methyl pyrrolidone, 2,3,4,5-tetrahydrothiophene-1,1-dioxide ("sulfolane"), 3-methylsulfolane and dimethyl sulfoxide, tetramethylenesulfone, mixtures thereof, and/or admixtures with water thereof.

A7. The process of any of A1 to A6, wherein:
  the membrane comprises a polyimide membrane, or a membrane comprising an ionic liquid.
A8. The process of any of A1 to A7, wherein:
  the first lean-solvent stream has a temperature in a range from 25 to 80° C. when fed into the membrane separator, and a positive pressure gradient of deltaP kPa exists from the first volume to the second volume of the membrane separator, and deltaP ranges from 345 to 10,342.
A9. The process of any of A1 to A8, wherein 0.01≤c(hcom)≤20.
A10. The process of A9, wherein 1≤c(hcom)≤15.
A11. The process of any of A1 to A10, further comprising:
  (A-9) feeding a second lean-solvent stream comprising the polar solvent into the extraction column.
A12. The process of A11, wherein in a given time period, the first lean-solvent stream comprises the polar solvent at a total weight of W1, the second lean-solvent stream comprises the polar solvent at a total weight of W2, and 0.5%≤W1/(W1+W2)*100%≤10%.
A13. The process of A12, wherein 0.5%≤W1/(W1+W2)*100%≤8%, preferably 0.5% W1/(W1+W2)*100%≤5%, more preferably 1%≤W1/(W1+W2)*100%≤5%, still more preferably 1%≤W1/(W1+W2)*100%≤3%.
A14. The process of A9 or A10, wherein the first lean-solvent stream and the second lean-solvent stream are derived from a common lean-solvent stream.
A15. The process of A14, wherein the common lean-solvent stream comprise the heavy components at a total concentration of c(hcom-cs) wt %, based on the total weight of the common lean-solvent stream, and the process further comprises:
  (A-10) monitoring c(hcom-cs); and
  (A-11) implementing step (A-3) to (A-8) only if c(hcom-cs)≤1.
A16. The process of any of A1 to A15, further comprising:
  (A-12) obtaining a bottoms stream from the extraction column, wherein the bottoms stream is rich in aromatic hydrocarbons and the polar solvent relative to the mixture feed;
  (A-13) separating at least a portion of the bottoms stream in a stripping column to obtain an aromatic hydrocarbons-rich stream comprising steam and depleted in the polar solvent relative to the bottoms stream, and a third lean-solvent stream depleted in aromatic hydrocarbons relative to the bottoms stream; and
  (A-14) deriving at least one of the first lean-solvent stream, the second lean-solvent stream, and the common lean-solvent stream from the third lean-solvent stream.
A17. The process of A16, further comprising:
  (A-15) deriving a fourth lean-solvent stream from the third lean-solvent stream;
  (A-16) regenerating the fourth lean-solvent stream in a steam stripping regeneration column and/or a vacuum regeneration column to obtain a regenerated lean-solvent stream comprising steam and a bottoms heavy stream; and
  (A-17) feeding the regenerated lean-solvent stream into one or more of: the stripping column, the extraction column, and the membrane separator as at least a portion of the first lean-solvent stream.
A18. The process of A17, further comprising:
  (A-18) condensing at least a portion of the aromatic hydrocarbons-rich stream to obtain a mixture comprising an aqueous liquid phase and an oil liquid phase;

(A-19) separating the aqueous liquid phase to obtain a water stream;

(A-20) heating the water stream to obtain a steam stream; and (A-21) feeding the steam stream to the steam stripping regeneration column and/or the vacuum regeneration column.

A19. The process of A18, wherein in step (A-21), the steam stream is at least partly heated by a portion of the third lean-solvent stream.

A20. A process for extracting aromatic hydrocarbons from a mixture feed comprising aromatic hydrocarbons and non-aromatic hydrocarbons, the process comprising:

(A-1) feeding the mixture feed into an extraction column;

(A-2) providing a first lean-solvent stream comprising a polar solvent at a concentration of c(ps) wt %, and heavy components at a total concentration of c(hcom) wt %, based on the total weight of the lean-solvent stream;

(A-3) feeding the first lean-solvent stream into a membrane separator, wherein: the membrane separator comprises a vessel having a first volume, a second volume, and a membrane between the first volume and the second volume; the first volume is separated from the second volume by the membrane; the membrane is more permeable to the polar solvent than to the heavy components; and the first lean-solvent stream is fed into the first volume;

(A-4) obtaining a retentate stream exiting the first volume of the membrane separator, wherein the retentate steam is rich in the heavy components relative to the first lean-solvent stream;

(A-5) obtaining a permeate stream exiting the second volume of the membrane separator, wherein the permeate stream is depleted in the heavy components relative to the first lean-solvent stream;

(A-6) feeding at least a portion of the permeate stream into the extraction column;

(A-9) feeding a second lean-solvent stream comprising the polar solvent into the extraction column, wherein in a given time period, the first lean-solvent stream comprises the polar solvent at a total weight of W1, the second lean-solvent stream comprises the polar solvent at a total weight of W2, and 0.5% W1/(W1+W2)*100%≤10%.

B1. A process for separating a mixture feed comprising aromatic hydrocarbons and non-aromatic hydrocarbons, the process comprising:

(B-1) feeding the mixture feed into a membrane separator, wherein: the membrane separator comprises a vessel having a first volume, a second volume, and a membrane between the first volume and the second volume; the first volume is separated from the second volume by the membrane; the membrane is more permeable to the aromatic hydrocarbons than to the non-aromatic hydrocarbons; and the mixture feed is fed into the first volume;

(B-2) obtaining a retentate stream exiting the first volume of the membrane separator, wherein the retentate steam is depleted in the aromatic hydrocarbons and rich in the non-aromatic hydrocarbons relative to the mixture feed; and (B-3) obtaining a permeate stream exiting the second volume of the membrane separator, wherein the permeate stream is rich in the aromatic hydrocarbons and depleted in the non-aromatic hydrocarbons relative to the mixture feed.

B2. The process of B1, further comprising:

(B-4) feeding at least a portion of the retentate stream and an extraction solvent stream into an extraction sub-system;

(B-5) obtaining from the extraction sub-system a non-aromatic hydrocarbons stream, an extracted aromatic hydrocarbons stream, and a lean-solvent stream; and (B-6) recycling at least a portion of the lean-solvent stream into the extraction sub-system as at least a portion of the extraction solvent stream.

B3. The process of B1 or B2, further comprising:

(B-7) feeding at least a portion of the permeate stream and at least a portion of the extracted aromatic hydrocarbon stream into an aromatic hydrocarbons distillation column; and (B-8) obtaining from the aromatic hydrocarbons distillation column two or more aromatic product streams.

B4. The process of B1 or B2, further comprising:

(B-9) feeding at least a portion of the permeate stream and/or a least a portion of the extracted aromatic hydrocarbon stream into a reactor; and (B-10) producing a converted product mixture from the reactor.

B5. The process of any of B1 to B4, wherein the mixture feed comprises benzene, toluene, non-aromatic hydrocarbon co-boilers of benzene, and non-aromatic hydrocarbon co-boilers of toluene at a total concentration thereof ≥60 wt %, based on the total weight of the mixture feed.

B6. The process of any of B1 to B5, further comprising:

(B-11) providing an isomerization feed stream consisting essentially of C8 aromatic hydrocarbons;

(B-12) contacting the isomerization feed stream with an isomerization catalyst in an isomerization zone under isomerization condition to produce an isomerization product mixture;

(B-13) separating the isomerization product mixture to obtain a C7− hydrocarbons-rich stream, and a C8+ hydrocarbon-rich stream; and (B-14) providing at least a portion of the C7− hydrocarbons-rich stream as the at least a portion of the mixture feed.

B6a. The process of B6, wherein the C7− hydrocarbons-rich stream is substantially free of C8 hydrocarbons.

B6b. The process of B6, wherein the C7− hydrocarbon-rich stream comprises C8 hydrocarbons at a concentration from c(C8)1 to c(C8)2 wt %, based on the total weight of the C7− hydrocarbon-rich stream, where c(C8)1 and c(C8)2 can be, independently, e.g., 0.5, 1, 2, 3, 4, 5, 6, 7, 8, 9, 10, 11, 12, 13, 14, 15, 16, 17, 18, 19, 20. Preferably c(C8)2≤10. Preferably c(C8)2≤5.

B7. The process of any of B1 to B6b, further comprising:

(B-15) providing a transalkylation feed mixture comprising C7− aromatic hydrocarbons and C9+ aromatic hydrocarbons;

(B-16) contacting the transalkylation feed mixture with a transalkylation catalyst in a transalkylation zone under transalkylation conditions to produce a transalkylation effluent;

(B-17) separating the transalkylation effluent to obtain a benzene-rich stream, and a C8 hydrocarbons-rich stream; and (B-18) providing at least a portion of the benzene-rich stream as the at least a portion of the mixture feed.

B8. The process of any of B1 to B7, further comprising:

(B-19) providing a toluene disproportionation feed consisting essentially of toluene;

(B-20) contacting the toluene disproportionation feed with a toluene disproportionation catalyst in a disproportionation zone under disproportionation conditions to produce a disproportionation effluent;

(B-21) separating the disproportionation effluent to obtain a benzene-rich stream, and a C8 hydrocarbons-rich stream; and (B-22) providing at least a portion of the benzene-rich stream as the at-least a portion of the mixture feed.

B9. The process of any of B5 to B8, wherein the mixture feed comprises ≥75 wt % of benzene and toluene combined, based on the total weight of the mixture feed.

B10. The process of B9, wherein the mixture feed comprising ≥90 wt % of benzene, based on the total weight of the mixture feed.

B11. The process of any of B1 to B3, wherein the mixture feed comprises benzene, toluene, C8 aromatic hydrocarbons, non-aromatic hydrocarbon co-boilers of benzene, non-aromatic hydrocarbon co-boilers of toluene, and non-aromatic hydrocarbon co-boilers of C8 aromatic hydrocarbons at a total concentration thereof ≥60 wt %, based on the total weight of the mixture feed.

B12. The process of any of B1 to B11, further comprising:
(B-23) providing a C6+hydrocarbons stream comprising benzene, non-aromatic benzene co-boilers, toluene, non-aromatic toluene co-boilers, C8 aromatic hydrocarbons, non-aromatic co-boilers of C8 aromatic hydrocarbons, and C9+ hydrocarbons;
(B-24) separating the C6+ hydrocarbons stream to obtain a C7− hydrocarbons stream rich in benzene and toluene, a C7− C8 hydrocarbons stream rich in C8 hydrocarbons, and a C9+ hydrocarbons stream rich in C9+ hydrocarbons;
(B-25) feeding at least a portion of the C7− hydrocarbon stream into the membrane separator as at least a portion of the mixture feed.

B13. The process of B12, further comprising:
(B-26) feeding at least a portion of the C7− hydrocarbon stream into the extraction sub-system column.

B14. The process of any of B1 to B13, further comprising:
(B-23) conducting away at least a portion of the retentate stream and/or at least a portion of the non-aromatic hydrocarbon stream.

B15. The process of B14, wherein in step (B-23), the at least a portion of the retentate stream and/or the at least a portion of the non-aromatic hydrocarbon stream is used as a mogas blending stock.

B16. The process of any of B1 to B15, further comprising:
(B-24) feeding at least a portion of the retentate stream into the extraction sub-system.

B17. The process of any of B1 to B16, wherein the polar solvent is selected from tetraethylene glycol, triethylene glycol, diethylene glycol, ethylene glycol, methoxy triglycol ether, diglycolamine, dipropylene glycol, N-formyl morpholine, N-methyl pyrrolidone, 2,3,4,5-tetrahydrothiophene-1,1-dioxide ("sulfolane"), 3-methylsulfolane and dimethyl sulfoxide, tetramethylenesulfone, mixtures thereof, and/or admixtures with water thereof.

B18. The process of any of B1 to B17, wherein the a mixture feed is in liquid phase.

C-1. A process for separating a mixture feed comprising aromatic hydrocarbons and non-aromatic hydrocarbons, the process comprising:
(C-1) feeding the mixture feed and a first lean-solvent stream comprising a polar solvent into an extraction column;

(C-2) obtaining an overhead stream and a bottoms stream from the extraction column, wherein the overhead stream is rich in non-aromatic hydrocarbons relative to the mixture feed, the bottoms stream is rich in aromatic hydrocarbons and the polar solvent relative to the mixture feed;

(C-3) feeding at least a portion of the bottoms stream into a membrane separator, wherein: the membrane separator comprises a vessel having a first volume, a second volume, and a membrane between the first volume and the second volume; the first volume is separated from the second volume by the membrane; the membrane is more permeable to the aromatic hydrocarbons than to the non-aromatic hydrocarbons; and the at least a portion of the bottoms stream is fed into the first volume;

(C-4) obtaining a retentate stream exiting the first volume of the membrane separator, wherein the retentate steam is depleted in the aromatic hydrocarbons and rich in the non-aromatic hydrocarbons relative to the bottoms stream;

(C-5) obtaining a permeate stream exiting the second volume of the membrane separator, wherein the permeate stream is rich in the aromatic hydrocarbons and depleted in the non-aromatic hydrocarbons relative to the bottoms stream; and (C-6) feeding at least a portion of the retentate stream to the extraction column.

C2. The process of C1, further comprising:
(C-7) obtaining at least an aromatic hydrocarbons-rich stream and a second lean-solvent stream from the permeate stream, wherein the second lean-solvent stream is rich in the polar solvent relative to the permeate steam; and
(C-8) recycling at least a portion of the second lean-solvent stream to the extraction column as at least a portion of the first lean-solvent stream.

C3. The process of C1 or C2, wherein the extraction column is an extraction distillation column.

C3a. The process of C3, wherein step (C-7) comprises feeding at least a portion of the permeate stream to a recovery distillation column, from which the aromatic hydrocarbons-rich stream and the second lean-solvent stream are obtained.

C4. The process of C1 or C2, wherein the extraction column is a liquid-liquid extraction column.

C4b. The process of C4, wherein step (C-7) comprises:
(C-7a) feeding at least a portion of the permeate stream to a stripping column, from which an overhead stream and a bottoms stream are produced, wherein the bottoms stream is rich in aromatic hydrocarbons and comprise the polar solvent;
(C-7b) feeding the bottoms stream from the stripping column to a recovery distillation column, from which the aromatic hydrocarbons-rich stream and the second lean-solvent stream are obtained.

C5. The process of any of C1 to C4b, wherein:
the polar solvent is selected from tetraethylene glycol, triethylene glycol, diethylene glycol, ethylene glycol, methoxy triglycol ether, diglycolamine, dipropylene glycol, N-formyl morpholine, N-methyl pyrrolidone, 2,3,4,5-tetrahydrothiophene-1,1-dioxide ("sulfolane"), 3-methylsulfolane and dimethyl sulfoxide, tetramethylenesulfone, mixtures thereof, and/or admixtures with water thereof.

C6. The process of any of C1 to C5, wherein:
the membrane comprises a polyimide membrane, or a membrane comprising an ionic liquid.

C7. The process of any of C1 to C6, wherein the mixture feed comprises ≥25 wt % of benzene and toluene combined, based on the total weight of the mixture feed.

C8. The process of any of C1 to C7, wherein the mixture feed comprises benzene, toluene, C8 aromatic hydrocarbons, non-aromatic hydrocarbon co-boilers of benzene, non-aromatic hydrocarbon co-boilers of toluene, and non-aromatic hydrocarbon co-boilers of the C8 aromatic hydrocarbons at a total concentration ≥60 wt %, based on the total weight of the mixture feed.

C9. The process of any of C1 to C8, further comprising:
(C-9) providing an isomerization feed stream consisting essentially of C8 aromatic hydrocarbons;
(C-10) contacting the isomerization feed stream with an isomerization catalyst in an isomerization zone under isomerization condition to produce an isomerization product mixture;
(C-11) separating the isomerization product mixture to obtain a C7− hydrocarbons-rich stream, and a C8+ hydrocarbon-rich stream; and
(C-12) providing at least a portion of the C7− hydrocarbons-rich stream as the at least a portion of the mixture feed.

C9a. The process of C9, wherein the C7− hydrocarbons-rich stream is substantially free of C8 hydrocarbons.

C9b. The process of C9, wherein the C7− hydrocarbon-rich stream comprises C8 hydrocarbons at a concentration from c(C8)1 to c(C8)2 wt %, based on the total weight of the C7− hydrocarbon-rich stream, where c(C8)1 and c(C8)2 can be, independently, e.g., 0.5, 1, 2, 3, 4, 5, 6, 7, 8, 9, 10, 11, 12, 13, 14, 15, 16, 17, 18, 19, 20. Preferably c(C8)2≤10. Preferably c(C8)2≤5.

C10. The process of any of C1 to C9b, further comprising:
(C-13) providing a transalkylation feed mixture comprising C7− aromatic hydrocarbons and C9+ aromatic hydrocarbons;
(C-14) contacting the transalkylation feed mixture with a transalkylation catalyst in a transalkylation zone under transalkylation conditions to produce a transalkylation effluent;
(C-15) separating the transalkylation effluent to obtain a benzene-rich stream, and a C8 hydrocarbons-rich stream; and
(C-16) providing at least a portion of the benzene-rich stream as the at least a portion of the mixture feed.

C11. The process of any of C1 to C10, further comprising:
(C-17) providing a toluene disproportionation feed consisting essentially of toluene;
(C-18) contacting the toluene disproportionation feed with a toluene disproportionation catalyst in a disproportionation zone under disproportionation conditions to produce a disproportionation effluent;
(C-19) separating the disproportionation effluent to obtain a benzene-rich stream, and a C8 hydrocarbons-rich stream; and
(C-20) providing at least a portion of the benzene-rich stream as the at-least a portion of the mixture feed.

C12. The process of any of C8 to C11, wherein the mixture feed comprises ≥75 wt % of benzene and toluene combined, based on the total weight of the mixture feed.

C13. The process of C12, wherein the mixture feed comprising ≥90 wt % of benzene, based on the total weight of the mixture feed.

C14. The process of any of C1 to C7, wherein the mixture feed comprises benzene, toluene, C8 aromatic hydrocarbons, non-aromatic hydrocarbon co-boilers of benzene, non-aromatic hydrocarbon co-boilers of toluene, and non-aromatic hydrocarbon co-boilers of C8 aromatic hydrocarbons at a total concentration thereof ≥60 wt %, based on the total weight of the mixture feed.

C15. The process of C14, further comprising:
(C-21) providing a C6+ hydrocarbons stream comprising benzene, non-aromatic benzene co-boilers, toluene, non-aromatic toluene co-boilers, C8 aromatic hydrocarbons, non-aromatic co-boilers of C8 aromatic hydrocarbons, and C9+ hydrocarbons;
(C-22) separating the C6+ hydrocarbons stream to obtain a C7− hydrocarbons stream rich in benzene and toluene, a C7− C8 hydrocarbons stream rich in C8 hydrocarbons, and a C9+ hydrocarbons stream rich in C9+ hydrocarbons;
(C-23) feeding at least a portion of the C7− hydrocarbon stream into the membrane separator as at least a portion of the mixture feed.

C16. The process of C15, further comprising:
(C-24) feeding at least a portion of the C7− hydrocarbon stream into the extraction sub-system column.

C17. The process of any of C1 to C16, further comprising:
(C-21) obtaining at least one non-aromatic hydrocarbon product stream from the overheads stream.

C18. The process of C17, wherein at least a portion of the non-aromatic hydrocarbon product stream is used as a mogas blending stock.

What is claimed is:

1. A process for extracting aromatic hydrocarbons from a mixture feed comprising aromatic hydrocarbons and non-aromatic hydrocarbons, the process comprising:
(A-1) feeding the mixture feed into an extraction column;
(A-2) receiving a first lean-solvent stream comprising a polar solvent at a concentration of c(ps) wt %, and heavy components at a total concentration of c(hcom) wt %; based on the total weight of the first lean-solvent stream, where 75≤c(ps)≤99.99, wherein heavy components comprise one or more components being present in the first lean-solvent stream different from the polar solvent;
(A-3) wherein the receiving comprises feeding the first lean-solvent stream into a membrane separator, wherein the membrane separator comprises a vessel having a first volume, a second volume, and a membrane between the first volume and the second volume; the first volume is separated from the second volume by the membrane; the membrane is more permeable to the polar solvent than to the heavy components; and the first lean-solvent stream is fed into the first volume;
(A-4) obtaining a retentate stream exiting the first volume of the membrane separator, wherein the retentate steam is rich in the heavy components relative to the first lean-solvent stream;
(A-5) obtaining a permeate stream exiting the second volume of the membrane separator, wherein the permeate stream is depleted in the heavy components relative to the first lean-solvent stream;
(A-6) feeding at least a portion of the permeate stream into the extraction column, wherein the permeate stream facilitates extraction of the aromatic hydrocarbons from the mixture feed;
(A-7) phase separating at least a portion of the retentate stream to obtain a heavy components stream and a solvent stream saturated with heavy components; and (A-8) feeding at least a portion of the solvent stream saturated with heavy components to the extraction column.

2. The process of claim 1, wherein the solvent stream saturated with heavy components comprises the heavy components at a total concentration in a range from 3 to 15 wt %, based on the total weight of the solvent stream saturated with the heavy components.

3. The process of claim 1, wherein:
the extraction column is an extraction distillation column.

4. The process of claim 1, wherein:
the extraction column is a liquid-liquid extraction column.

5. The process of claim 1, wherein:
the polar solvent is selected from tetraethylene glycol, triethylene glycol, diethylene glycol, ethylene glycol, methoxy triglycol ether, diglycolamine, dipropylene glycol, N-formyl morpholine, N-methyl pyrrolidone, 2,3,4,5-tetrahydrothiophene-1,1-dioxide ("sulfolane"), 3-methylsulfolane and dimethyl sulfoxide, tetramethylenesulfone, mixtures thereof, and/or admixtures with water thereof.

6. The process of claim 1, wherein:
the membrane comprises a polyimide membrane, and/or a membrane comprising an ionic liquid.

7. The process of claim 1, wherein:
the first lean-solvent stream has a temperature in a range from 25 to 80° C. when fed into the membrane separator, and a positive pressure gradient of deltaP kPa exists from the first volume to the second volume of the membrane separator, and delta ranges from 345 to 10,342 kilopascal.

8. The process of claim 1, wherein $0.01 \leq c(hcom) \leq 20$.

9. The process of claim 8, wherein $1 \leq c(hcom) \leq 15$.

10. The process of claim 1, further comprising:
(A-9) feeding a second lean-solvent stream comprising the polar solvent into the extraction column, wherein the first and second lean-solvent stream are portions of a common lean-solvent stream.

11. The process of claim 10, wherein in a given time period, the first lean-solvent stream comprises the polar solvent at a total weight of the second lean-solvent stream comprises the polar solvent at a total weight of W2, and $0.5\% \leq W1/(W1+W2)*100\% \leq 10\%$.

12. The process of claim 11, wherein $0.5\% \leq W1/(W1+W2)*100\% \leq 8\%$.

13. The process of claim 10, wherein the common lean-solvent stream is a recycle solvent stream produced from a distillation column.

14. The process of claim 13, wherein the common lean-solvent stream comprise the heavy components at a total concentration of c(hcom-cs) wt %, based on the total weight of the common lean-solvent stream, and the process further comprises:
(A-10) monitoring c(hcom-cs); and
(A-11) implementing step (A-3) to (A-8) only if $c(hcom-cs) \geq 1$.

15. The process of claim 1, further comprising:
(A-12) obtaining a bottoms stream from the extraction column, wherein the bottoms stream is rich in aromatic hydrocarbons and the polar solvent relative to the mixture feed;
(A-13) separating at least a portion of the bottoms stream in a stripping column to obtain an aromatic hydrocarbons-rich stream comprising steam and depleted in the polar solvent relative to the bottoms stream, and a third lean-solvent stream depleted in aromatic hydrocarbons relative to the bottoms stream; and (A-14) deriving at least one of the first lean-solvent stream, a second lean-solvent stream, and a common lean-solvent stream from the third lean-solvent stream.

16. The process of claim 15, further comprising:
(A-15) deriving a fourth lean-solvent stream from the third lean-solvent stream;
(A-16) regenerating the fourth lean-solvent stream in a steam stripping regeneration column and/or a vacuum regeneration column to obtain a regenerated lean-solvent stream comprising steam and a bottoms heavy stream; and
(A-17) feeding the regenerated lean-solvent stream into one or more of the stripping column, the extraction column, and the membrane separator as at least a portion of the first lean-solvent stream.

17. The process of claim 16, further comprising:
(A-18) condensing at least a portion of the aromatic hydrocarbons-rich stream to obtain a mixture comprising an aqueous liquid phase and an oil liquid phase;
(A-19) separating the aqueous liquid phase to obtain a water stream;
(A-20) heating the water stream to obtain a steam stream; and
(A-21) feeding the steam stream to the steam stripping regeneration column.

18. The process of claim 17, wherein in step (A-21), the steam stream is at least partly heated by a portion of the third lean-solvent stream.

19. A process for extracting aromatic hydrocarbons from a mixture feed comprising aromatic hydrocarbons and non-aromatic hydrocarbons, the process comprising:
(A-1) feeding the mixture feed into an extraction column;
(A-2) receiving a first lean-solvent stream comprising a polar solvent at a concentration of c(ps) wt %, and heavy components at a total concentration of c(hcom) wt %, based on the total weight of the lean-solvent stream, wherein heavy components comprise one or more components being present in the first lean-solvent stream different from the polar solvent;
(A-3) wherein the receiving comprises feeding the first lean-solvent stream into a membrane separator, wherein the membrane separator comprises a vessel having a first volume, a second volume, and a membrane between the first volume and the second volume; the first volume is separated from the second volume by the membrane; the membrane is more permeable to the polar solvent than to the heavy components; and the first lean-solvent stream is fed into the first volume;
(A-4) obtaining a retentate stream exiting the first volume of the membrane separator, wherein the retentate steam is rich in the heavy components relative to the first lean-solvent stream;
(A-5) obtaining a permeate stream exiting the second volume of the membrane separator, wherein the permeate stream is depleted in the heavy components relative to the first lean-solvent stream;
(A-6) feeding at least a portion of the permeate stream into the extraction column, wherein the permeate stream facilitates extraction of the aromatic hydrocarbons from the mixture feed;
(A-7) phase separating at least a portion of the retentate stream to obtain a heavy components stream and a solvent stream saturated with heavy components; and
(A-8) feeding at least a portion of the solvent stream saturated with heavy components to the extraction column;

(A-9) feeding a second lean-solvent stream comprising the polar solvent into the extraction column, wherein in a given time period, the first lean-solvent stream comprises the polar solvent at a total weight of W1, the second lean-solvent stream comprises the polar solvent at a total weight of W2, and $0.5\% \leq W1/(W1+W2)*100\% \leq 10\%$.

* * * * *